(12) United States Patent
Doles et al.

(10) Patent No.: US 12,569,359 B2
(45) **Date of Patent: *Mar. 10, 2026**

(54) SYSTEM FOR RESIDUAL LIMBS OF AMPUTEES

(71) Applicant: JSG IP Ventures, LLC, Greenwood Village, CO (US)

(72) Inventors: Jordan T. Doles, Fort Collins, CO (US); Paul Goudreau, Edina, MN (US); Troy Winsand, Maple Grove, MN (US); Mark Hatcher, Golden Valley, MN (US); Gary McAdam, Highlands Ranch, CO (US)

(73) Assignee: JSG IP Ventures, LLC, Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/232,555

(22) Filed: Jun. 9, 2025

(65) Prior Publication Data

US 2026/0053646 A1     Feb. 26, 2026

Related U.S. Application Data

(63) Continuation of application No. 18/810,416, filed on Aug. 20, 2024, now Pat. No. 12,324,754.

(51) Int. Cl.
A61F 2/78          (2006.01)
A61F 2/70          (2006.01)
(Continued)

(52) U.S. Cl.
CPC .............. A61F 2/7812 (2013.01); A61F 2/70 (2013.01); A61F 2/72 (2013.01); A61N 1/361 (2013.01); A61F 2002/5059 (2013.01); *A61F* *2002/5061* (2013.01); *A61F 2002/5063* (2013.01); *A61F 2002/5064* (2013.01); *A61F* *2002/6827* (2013.01); *A61F 2002/704* (2013.01); *A61F 2002/705* (2013.01); *A61F* *2002/707* (2013.01);
(Continued)

(58) Field of Classification Search
None
See application file for complete search history.

(56) References Cited

U.S. PATENT DOCUMENTS

| | | | |
|---|---|---|---|
| 11,039,941 B2 | 6/2021 | Friesen et al. | |
| 12,324,754 B1 * | 6/2025 | Doles | A61F 2/72 |

(Continued)

FOREIGN PATENT DOCUMENTS

DE     20 2017 007 073 U1 *  7/2019  ............... A61F 2/68

OTHER PUBLICATIONS

Patent Translation of WO2019025838A1, Andreas et al (Year: 2019).

*Primary Examiner* — David H Willse
(74) *Attorney, Agent, or Firm* — Holland & Hart LLP

(57) ABSTRACT

Various aspects of this disclosure relate to a layered polymer substrate with electrodes and conductive ink embedded in the substrate. In some embodiments, a prosthetic liner may be bonded onto the polymer substrate. The substrate may include an interconnect coupled to the electrodes via the conductive ink. The system may include a controller (e.g., an electrode controller) in communication with the electrodes via the conductive ink. The electrodes may be activated such that they may stimulate nerve fibers in a user's residual limb.

20 Claims, 24 Drawing Sheets

(51) Int. Cl.

| | |
|---|---|
| *A61F 2/72* | (2006.01) |
| *A61N 1/36* | (2006.01) |
| A61F 2/50 | (2006.01) |
| A61F 2/68 | (2006.01) |
| A61F 2/76 | (2006.01) |

(52) U.S. Cl.

CPC ... *A61F 2002/768* (2013.01); *A61F 2002/769* (2013.01); *A61F 2002/7818* (2013.01); *A61F 2002/785* (2013.01)

(56) References Cited

U.S. PATENT DOCUMENTS

| | | | |
|---|---|---|---|
| 12,329,969 B1 * | 6/2025 | Doles ................... | A61N 1/0476 |
| 2006/0190057 A1 | 8/2006 | Reese | |
| 2009/0079550 A1 | 3/2009 | Makinen et al. | |
| 2010/0049450 A1 | 2/2010 | Nagakubo et al. | |
| 2012/0191220 A1 | 7/2012 | Bedard et al. | |
| 2013/0046394 A1 | 2/2013 | Lipschutz et al. | |
| 2015/0032174 A1 | 1/2015 | Ghosh | |
| 2017/0231520 A1 | 8/2017 | Yang | |
| 2018/0178008 A1 | 6/2018 | Bouton et al. | |
| 2019/0021883 A1 | 1/2019 | Herr et al. | |
| 2020/0179694 A1 | 6/2020 | Kong et al. | |
| 2021/0069458 A1 * | 3/2021 | Perry ........................ | A61F 2/80 |
| 2021/0244941 A1 | 8/2021 | Daniels et al. | |
| 2022/0031245 A1 | 2/2022 | Bresler | |
| 2022/0409403 A1 * | 12/2022 | Brandstätter .......... | A61B 5/486 |
| 2024/0225859 A1 | 7/2024 | Podhola | |
| 2024/0252327 A1 * | 8/2024 | Doles ................... | A61N 1/3606 |

* cited by examiner

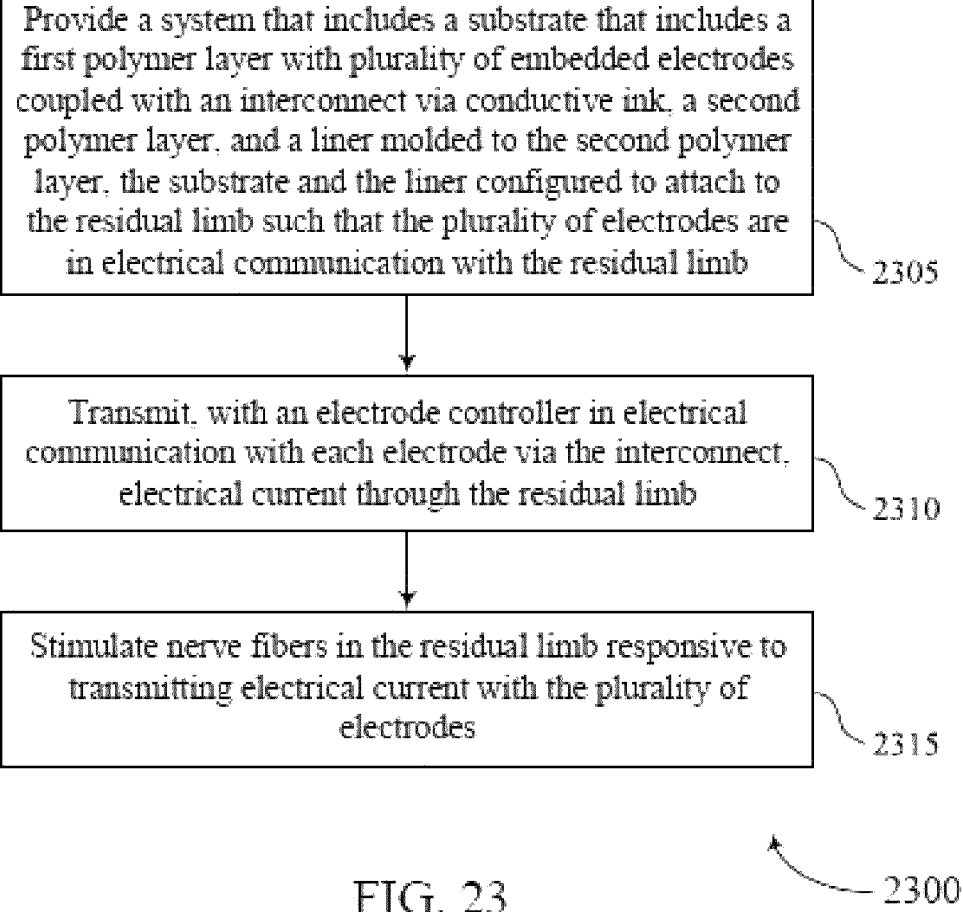

Provide a system that includes a substrate that includes a first polymer layer with plurality of embedded electrodes coupled with an interconnect via conductive ink, a second polymer layer, and a liner molded to the second polymer layer, the substrate and the liner configured to attach to the residual limb such that the plurality of electrodes are in electrical communication with the residual limb
~2305

Transmit, with an electrode controller in electrical communication with each electrode via the interconnect, electrical current through the residual limb
~2310

Stimulate nerve fibers in the residual limb responsive to transmitting electrical current with the plurality of electrodes
~2315

FIG. 23          ~2300

Figure 24:
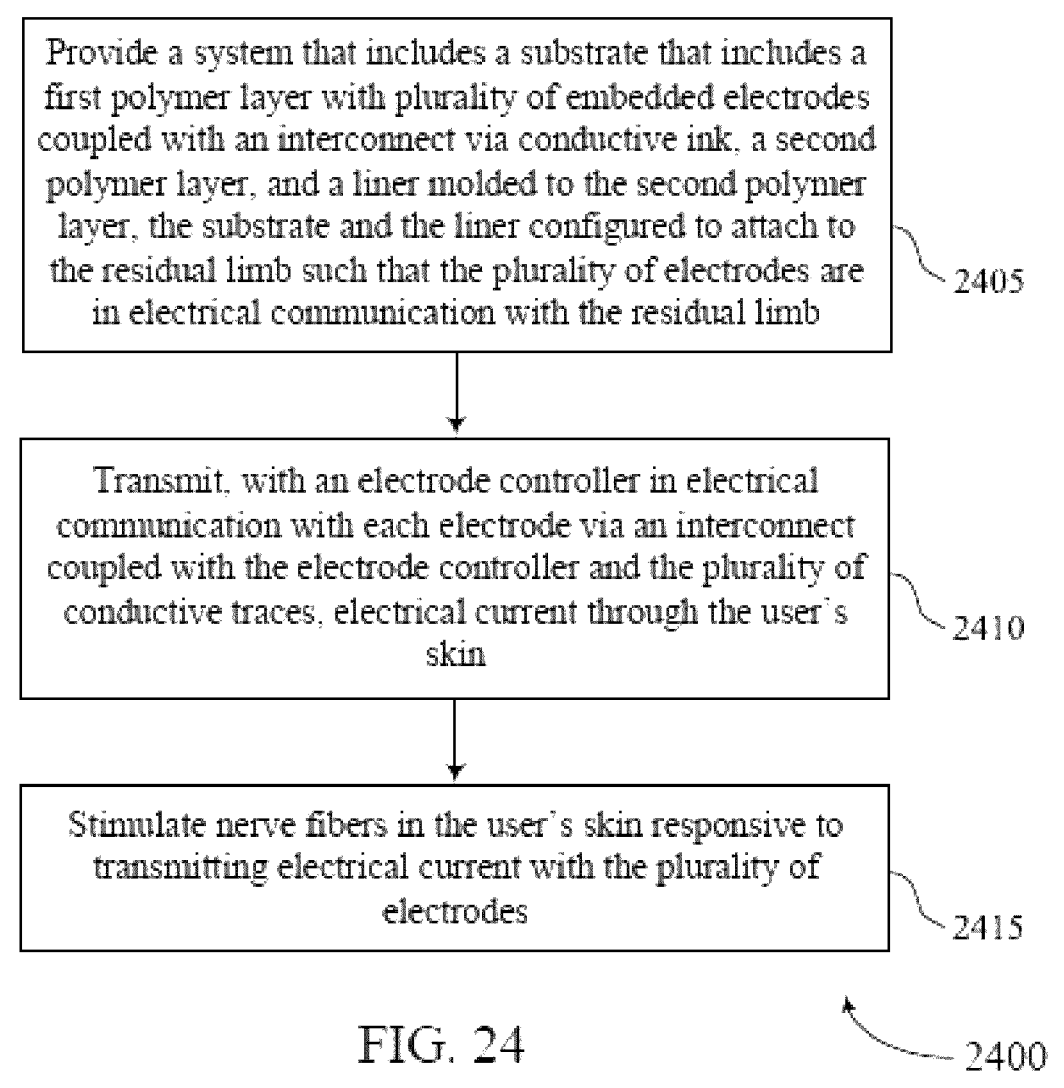

Provide a system that includes a substrate that includes a first polymer layer with plurality of embedded electrodes coupled with an interconnect via conductive ink, a second polymer layer, and a liner molded to the second polymer layer, the substrate and the liner configured to attach to the residual limb such that the plurality of electrodes are in electrical communication with the residual limb

2405

Transmit, with an electrode controller in electrical communication with each electrode via an interconnect coupled with the electrode controller and the plurality of conductive traces, electrical current through the user's skin

2410

Stimulate nerve fibers in the user's skin responsive to transmitting electrical current with the plurality of electrodes

SYSTEM FOR RESIDUAL LIMBS OF AMPUTEES

CROSS-REFERENCE TO RELATED APPLICATIONS

This patent application is a Continuation of U.S. patent application Ser. No. 18/810,416 and U.S. Pat. No. 12,324, 754, entitled "SYSTEM FOR RESIDUAL LIMBS OF AMPUTEES," filed Aug. 20, 2024, the disclosure of which is hereby incorporated by reference in its entirety.

BACKGROUND

Amputees frequently suffer from phantom limb pain, phantom limb syndrome, residual limb pain, general soreness, muscular atrophy, pain-related impairment and other symptoms in which they experience sensations that they attribute to a missing limb. These sensations are generally undesirable, frequently painful, and, in some cases, debilitating. The onset of these sensations often occurs after surgery and can last from seconds to minutes, to hours, or to days. For some amputees, these sensations last for years. Pain from these sensations can interfere with the physical and psychosocial rehabilitation of the amputee. As a result, quality of life is compromised.

Management of these sensations may include pain medication and medication directed toward interrupting pain signals in an amputee's brain or spinal cord as well as non-medication therapies which work an amputee's brain's interpretation of these signals. For example, NSAIDs, opioids, antidepressants, anticonvulsants, beta-blockers and muscle relaxants may be taken alone or in combination. These traditional therapies can offer temporary relief yet often have negative side effects and decreased effectiveness over time. Complementary therapies can include acupuncture, massage of the residual limb, mirror box therapy, biofeedback, and psychological therapy to improve functional outcome and well-being but do not address the underlying neural mechanisms driving the pain or sensations.

Other non-pharmacological interventions to reduce symptoms of phantom limb syndrome remain desirable.

SUMMARY

Various aspects of this disclosure relate to the finding that neural feedback from interactions with a substrate and/or liner on a residual limb can help alleviate symptoms of phantom limb pain, phantom limb syndrome, residual limb pain, general soreness, muscular atrophy, pain-related impairment and other related symptoms after an amputation.

Some embodiments relate to apparatus for modulating nerve activation in a residual limb of an amputee. The apparatus may include a substrate configured to contact the residual limb and may include a first polymer layer including a plurality of embedded electrodes and conductive ink, and a second polymer layer, and a liner bonded to the second polymer layer, wherein the substrate and the liner are configured to receive the residual limb, such that at least one of the plurality of embedded electrodes is in electrical communication with the residual limb and configured such that transmitting electrical current through the residual limb, with a controller in electrical communication with each electrode via the conductive ink, stimulates nerve fibers in the residual limb.

Some embodiments relate to apparatus for modulating nerve activation. The apparatus may include a substrate comprising: a first polymer layer including a plurality of embedded electrodes; a second polymer layer, and a plurality of conductive traces comprising a conductive ink coupled with the plurality of embedded electrodes, wherein the substrate is configured such that at least one of the plurality of embedded electrodes is in electrical communication with a user's skin and the plurality of embedded electrodes are configured such that transmitting electrical current through the user's skin, with a controller in electrical communication with each electrode via the plurality of conductive traces, stimulates nerve fibers in the user's skin.

Some embodiments relate to methods of modulating nerve activation in a residual limb of an amputee. The method may include providing a system that comprises: a substrate comprising: a first polymer layer with plurality of embedded electrodes coupled with an interconnect via conductive ink, a second polymer layer; and a liner molded to the second polymer layer, the substrate and the liner configured to attach to the residual limb such that the plurality of electrodes are in electrical communication with the residual limb, transmitting, with an electrode controller in electrical communication with each electrode via the interconnect, electrical current through the residual limb; and stimulating nerve fibers in the residual limb responsive to transmitting electrical current with the plurality of electrodes.

Some embodiments relate to methods of modulating nerve activation. The method may include providing a system that comprises: a substrate comprising: a first polymer layer including: a plurality of electrodes coupled with a plurality of conductive traces comprising conductive ink, and a second polymer layer; the substrate configured to attach to a user's skin such that the plurality of electrodes is in electrical communication with the user's skin, transmitting, with an electrode controller in electrical communication with each electrode via an interconnect coupled with the electrode controller and the plurality of conductive traces, electrical current through the user's skin, and stimulating nerve fibers in the user's skin responsive to transmitting electrical current with the plurality of electrodes.

Some embodiments relate to methods of forming a substrate and liner. The method may include forming a substrate, including: forming a first polymer layer comprising a plurality of electrodes, providing a plurality of conductive paths to the plurality of electrodes, wherein each electrode is associated with a respective conductive path to an interconnect, forming, over the first polymer layer and the plurality of conductive paths, a second polymer layer, wherein the plurality of electrodes are embedded in the substrate relative to an upper surface of the second silicone layer; and molding a liner to the second polymer layer.

Some embodiments relate to methods of forming a substrate. The method may include forming a substrate, including: forming a first polymer layer comprising a plurality of electrodes, forming a plurality of conductive paths to the plurality of electrodes configured to connect with an interconnect, wherein each electrode is associated with a respective conductive path, forming, over the first polymer layer and the plurality of conductive paths, a second polymer layer, wherein the plurality of electrodes are embedded relative to an upper surface of the second polymer layer.

Some embodiments relate to a non-transitory computer-readable medium storing instructions. The non-transitory computer-readable medium storing instructions, when executed by one or more processors of a system, cause the system to receive, at a user device, a first indication to transmit electrical current through a user's skin via a plurality of electrodes of a polymer substrate that are in electrical contact with the user's skin, wherein the plurality of electrodes are coupled with respective conductive traces via conductive ink, wherein the first indication is associated with a first sensation for stimulating the user's skin; and transmit, to a switching matrix of the user device, signaling indicating to transmit electrical current through the user's skin, using the first sensation, via one or more subsets of the plurality of electrodes.

Some embodiments relate to a system for modulating nerve activation in a residual limb of an amputee. The system may include a substrate configured to contact the residual limb, including: a first polymer layer including a plurality of embedded electrodes, a plurality of conductive ink traces printed on the first polymer layer and coupled with each of the plurality of embedded electrodes, a plurality of channels above the first polymer layer, each channel of the plurality of channels associated with a respective conductive ink trace, and a second polymer layer over the first polymer layer, the plurality of conductive ink traces, and the plurality of channels, an interconnect comprising a plurality of pins configured to connect to the conductive ink traces via a respective channel of the plurality of channels, an electronic controller coupled with the interconnect and configured for electrical communication with each electrode of the plurality of embedded electrodes via a respective conductive ink trace, and a liner bonded to the second polymer layer, wherein the substrate and the liner are configured to receive the residual limb such that at least one of the plurality of embedded electrodes is in electrical communication with the residual limb and configured such that transmitting electrical current through the residual limb, with the electronic controller in electrical communication with each electrode via the conductive ink traces, stimulates nerve fibers in the residual limb.

Various other aspects of the inventions of this disclosure will become apparent upon review of the following detailed description and claims. The scope of this disclosure shall not be limited by the foregoing summary and background. The scope of each patent claim that matures from this disclosure shall not be limited by the foregoing summary and background or by the following detailed description, and the scope of each patent claim that matures from this disclosure shall instead be limited solely by the explicit language of the claim in the context of its claim dependency.

BRIEF DESCRIPTION OF THE DRAWINGS

FIGS. 13, 14a, 14b, and 15 depict an external interconnect coupled with a substrate that supports nerve modulation as described herein.

FIGS. 23 and 24 are flowcharts illustrating methods that depict use of the system.

DETAILED DESCRIPTION

Figure 1:
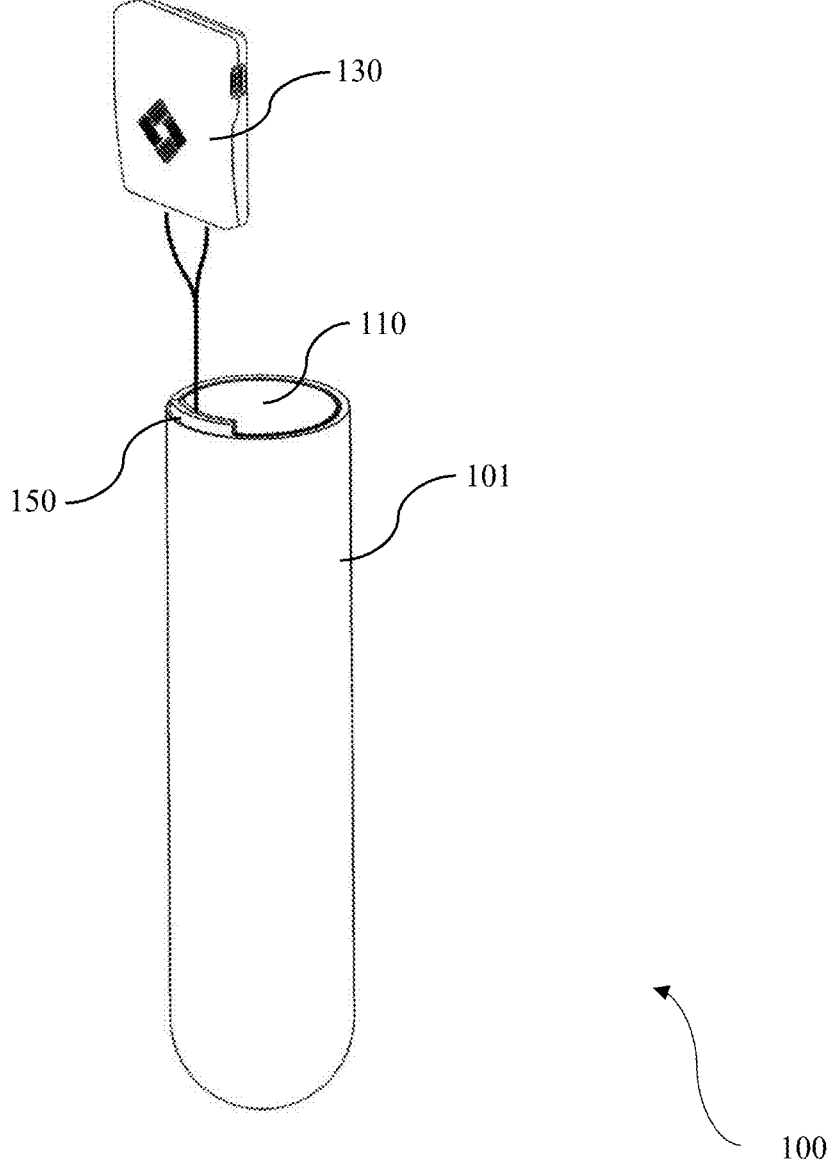
FIGS. 1 and 2 depict systems that support nerve modulation as described herein.

The disclosed technology includes systems and methods to treat post-amputation and post-operative related conditions and symptoms, including Phantom Limb Syndrome (PLS), Phantom Limb Pain (PLP), Residual Limb Pain, and muscular atrophy, and to increase an amputee's proprioceptive senses of a prosthetic limb.

Various aspects of this disclosure relate to a polymer (e.g., silicone) substrate comprising one or more electrodes that are configured to transmit electrical current through a residual limb of an amputee. Different interactions with the substrate cause different activation of the electrodes to transmit electrical current through different areas of the residual limb and modulate neurons differently within the residual limb. As a result of the interactions with the substrate, electrical stimulation to underlying nerve fibers provide an amputee the ability to feel a stimulus. The stimuli, alone or in combination with other treatment applications (e.g., artificial visualization, such as mirror therapy), can evoke a somatic sensation. As a result, the amputee may perceive the missing limb is intact and/or functional, which can decrease or resolve the condition or symptom, such as PLP.

In some embodiments, interactions with the substrate are any interactions, events, or modalities sensed by sensors that cause activation of the electrodes. In some embodiments, a modality is a touch modality, such as touch, force, pressure, flutter, or vibration. In other examples, the electrodes may be activated through use of an application, such as an application on a mobile device or a device that is connected (e.g., physically connected) to the substrate.

Various aspects of this disclosure relate to a system for use by an amputee. In some embodiments, the system is for modulating nerve activation in a residual limb of an amputee.

In some embodiments, the system comprises a polymer (e.g., silicone) substrate. In some specific embodiments, the system comprises a substrate that comprises electrodes. In some very specific embodiments, the system comprises a substrate that comprises embedded electrodes. In some embodiments, the system comprises a liner bonded to a polymer (e.g., silicone) substrate.

Any medical-grade electrode capable of conducting at least 30 milliamps of pulsed electrical current is generally suitable for use with the systems and methods described herein. In some specific embodiments, an electrode is suitable for electronic muscle stimulation. In some specific embodiments, an electrode is suitable for transcutaneous electrical nerve stimulation. In some specific embodiments, electrodes are suitable for both electronic muscle stimulation and transcutaneous electrical nerve stimulation. In some very specific embodiments, an electrode is a carbon rubber electrode.

In some specific embodiments, an electrode is suitable for nerve stimulation specific to the C fibers using impulses with varying geometries and duration. More specifically, the electrical current transforms pain signals into non-pain signals. In some embodiments, the electrodes may be placed on the skin above and below where pain is experienced to capture the nerve endings and replace signals from the area experiencing pain with signals coming from adjacent areas experiencing no pain. As a result, the pain signals sent to the brain are scrambled.

The electrodes of this disclosure are generally suitable for continuous, long-term contact with human skin, which contact is optionally mediated by a conductive product (e.g., gel). In some embodiments, continuous, long-term contact refers to at least two hours of continuous contact. In some specific embodiments, continuous, long-term contact refers to at least twelve hours of continuous contact. In some very specific embodiments, continuous, long-term contact refers to at least 48 hours of continuous contact.

In some embodiments, the substrate or the liner bonded to the substrate is a single, unified structure. In some specific embodiments, the substrate or the liner bonded to the substrate is a single, unified structure in which the electrodes are embedded. In some very specific embodiments, the substrate or the liner bonded to the substrate is a single, unified structure in which the electrodes and conductive traces are embedded, wherein each electrode of the electrodes is connected to at least one conductive trace such that the conductive traces can mediate electrical communication between the electrodes and a controller. The electrodes may be adapted to respective conductive traces to create electrical communication between the electrodes and the conductive traces.

The liner or the substrate is generally configured to receive a residual limb of an amputee. In some specific embodiments, the liner or the substrate is configured to receive the residual limb such that each electrode of the electrodes is in electrical communication with the residual limb. A conductive gel may be applied, for example, between the electrodes and a residual limb to facilitate electrical communication between the electrodes and the residual limb.

In some embodiments, each electrode is paired with at least one other electrode such that, when the electrodes is in electrical communication with the residual limb, then each electrode can (1) transmit electrical current through the residual limb both to a first negative electrode with which the electrode is paired and, independently, to a second negative electrode with which the electrode is paired and/or (2) receive electrical current through the residual limb from both a first positive electrode with which the electrode is paired and, independently, from a second positive electrode with which the electrode is paired. In such embodiments, each electrode can transfer electrical current through and/or receive electrical current from at least one other electrode to provide different paths of electrical current through the residual limb, for example, in response to different sensors and/or to differentially modulate nerve fibers in the residual limb.

In some embodiments, the system is configured such that when (1) two or more electrodes are activated and (2) the two or more electrodes are in electrical communication with the residual limb, then one electrode of the activated two or more electrodes transmits electrical current through the residual limb and another electrode of the activated two or more electrodes receives the electrical current that is transmitted through the residual limb. In some specific embodiments, the system is configured such that when (1) two electrodes are activated and (2) the two electrodes are in electrical communication with the residual limb, then one electrode of the activated two electrodes transmits electrical current through the residual limb and the other electrode of the activated two electrodes receives the electrical current that is transmitted through the residual limb. An electrode is activated when the electrode is transmitting or receiving electrical current.

In some embodiments, the system comprises a controller (e.g., an electrode controller) in electrical communication with each electrode of the electrodes. In some embodiments, the controller is configured to control whether each electrode can transmit electrical current to a negative electrode. In some embodiments, the controller is configured to control whether each electrode can receive electrical current from a positive electrode. In some specific embodiments, the controller is configured to control both whether each electrode that can transmit electrical current transmits the electrical current to a negative electrode and whether each electrode that can receive electrical current receives the electrical current from a positive electrode. A controller can therefore control which electrodes of the electrodes transmit and receive electrical current, for example, in response to different sensors or signals received (e.g., from a mobile application) and/or to transmit electrical current through different regions of the residual limb.

In some embodiments, the controller is configured to control whether each electrode that can transmit electrical current transmits the electrical current through the residual limb to one or both of a first negative electrode and a second negative electrode. In some embodiments, the electrode controller is configured to control whether each electrode that can receive electrical current receives the electrical current from one or both of a first positive electrode and a second positive electrode. In some specific embodiments, the electrode controller is configured to control both whether each electrode that can transmit electrical current transmits the electrical current through the residual limb to one or both of a first negative electrode and a second negative electrode and whether each electrode that can receive electrical current receives the electrical current from one or both of a first positive electrode and a second positive electrode.

In some embodiments, the electrode controller controls the electrical current transmitted or received by each electrode.

In some embodiments, the system is configured such that transmitting and receiving electrical current through the residual limb modulates nerve fibers in the residual limb. In some specific embodiments, the system is configured such that transmitting and receiving electrical current through the residual limb stimulates nerve fibers in the residual limb. In some very specific embodiments, the system is configured such that transmitting and receiving electrical current through the residual limb stimulates myelinated Aβ nerve fibers in the residual limb. In some very specific embodiments, the system is configured such that transmitting and receiving electrical current through the residual limb modulates the activation of myelinated Aδ nerve fibers in the residual limb. In some very specific embodiments, the system is configured such that transmitting and receiving electrical current through the residual limb modulates the activation of unmyelinated C nerve fibers in the residual limb.

In some embodiments, each electrode of the electrodes is configured such that transmitting and receiving electrical current through the residual limb modulates nerve fibers in the residual limb. In some specific embodiments, each electrode of the electrodes is configured such that transmitting and receiving electrical current through the residual limb stimulates nerve fibers in the residual limb. In some very specific embodiments, each electrode of the electrodes is configured such that transmitting and receiving electrical current through the residual limb stimulates myelinated Aβ nerve fibers in the residual limb. In some very specific embodiments, each electrode of the electrodes is configured such that transmitting and receiving electrical current through the residual limb modulates the activation of myelinated Aδ nerve fibers in the residual limb. In some very specific embodiments, each electrode of the electrodes is configured such that transmitting and receiving electrical current through the residual limb modulates the activation of unmyelinated C nerve fibers in the residual limb.

In some embodiments, the electrical current is pulsed electrical current. In some embodiments, the pulsed electrical current has a pulse frequency of at least 2 and up to 200 pulses per second. In some specific embodiments, the pulsed electrical current has a pulse frequency of at least 20 and up to 180 pulses per second. In some very specific embodiments, the pulsed electrical current has a pulse frequency of at least 135 and up to 155 pulses per second.

In some embodiments, the pulsed electrical current has a pulse width of up to 400 microseconds. In some specific embodiments, the pulsed electrical current has a pulse width of up to 100 microseconds. In some very specific embodiments, the pulsed electrical current has a pulse width of up to 50 microseconds.

In some embodiments, the pulsed electrical current has an amplitude of up to 150 milliamps. In some specific embodiments, the pulsed electrical current has an amplitude of up to 100 milliamps. In some very specific embodiments, the pulsed electrical current has an amplitude of at least 10 and up to 30 milliamps.

In some embodiments, the electrodes may be positioned in an array of one or more electrodes.

In some embodiments, the system comprises one or more electrodes that are not included in the array of electrodes. The unincluded one or more electrodes may be, for example, electrodes that are not used to transmit and/or receive electrical current to and/or from a residual limb or electrodes that a prospective infringer of one or more patent claims that mature from this disclosure might contemplate including in a system in an attempt to develop a legal theory of non-infringement.

The electrodes may be assembled in various configurations. For example, in some embodiments, the electrodes comprise one or more of, an anterior-proximal electrode, an anterior-distal electrode, a lateral-proximal electrode, a lateral-distal electrode, a posterior-proximal electrode, a posterior-distal electrode, a medial-proximal electrode, and a medial-distal electrode. More specifically, in some embodiments, the electrodes comprise one or more of an anterior-lateral-proximal electrode, a posterior-lateral-proximal electrode, an anterior-lateral-distal electrode, a posterior-lateral-distal electrode, an anterior-medial-proximal electrode, a posterior-medial-proximal electrode, an anterior-medial-distal electrode, and a posterior-medial-distal electrode.

In some embodiments, the system comprises a controller, wherein the controller is in communication with the electrodes such that the controller can bypass the sensors to cause each electrode to transmit or receive electrical current to or from a residual limb of an amputee when the electrode is in electrical communication with the residual limb. Such a controller can allow an amputee to transmit electrical current through his or her residual limb when the amputee is not wearing a prosthesis with the cover, for example, after the amputee has removed such a prosthesis to sleep. A controller can also allow an amputee to run programs that specifically treat phantom limb syndrome. An amputee might develop a specific pattern of transmitting electrical current through his or her residual limb that is particularly efficacious at treating phantom limb syndrome, the system might track an amputee's use of the system and develop a specific pattern that displays a high probability of efficaciously treating phantom limb syndrome, or crowd-sourced use records from a plurality of amputees or other data might identify a specific pattern that displays a high probability of efficaciously treating phantom limb syndrome, and a program on a controller can drive the f electrodes to implement the specific pattern. Such a controller may optionally be an electrode controller or a secondary controller as described herein.

In some embodiments, the secondary controller is a computing device. In some specific embodiments, the secondary controller is a mobile computing device. In some very specific embodiments, the secondary controller is a cell phone. In other embodiments, the secondary controller is a wearable device configured to communicate with the substrate via a Wi-Fi or Bluetooth connection.

In some embodiments, the secondary controller is in wireless communication with the electrodes. In some specific embodiments, the secondary controller is in wireless communication with an electrode controller. In some very specific embodiments, the secondary controller is in wireless communication with an electrode controller that controls the electrodes.

In some embodiments, the wireless communication is mediated by one or both of a Bluetooth or Wi-Fi connection between the secondary controller and the electrodes. In some specific embodiments, the wireless communication is mediated by one or both of a Bluetooth or Wi-Fi connection between the secondary controller and the electrodes, which is mediated by an electrode controller that controls the electrodes.

In some embodiments, the secondary controller is in wireless communication with the electrode controller.

In some embodiments, the substrate may be configured to contact a residual limb of an amputee. The substrate may be configured to transmit an electrical current through the residual limb using one or more electrodes (e.g., an array of electrodes). The electrodes may be coupled with an interconnect (e.g., a silicone interconnect, a rigid silicone interconnect) via a conductive material, such as respective conductive traces. In some embodiments, the conductive traces may include a conductive ink that is configured to communicate signaling (e.g., from a controller or source external to the substrate) that activates (e.g., engages, turns on) one or more of the electrodes. The electrodes, when activated, may stimulate nerve fibers in the residual limb of the amputee.

In some embodiments, a liner may be bonded to the substrate. The substrate and/or the liner may include biocompatible materials. Additionally or alternatively, the substrate and the liner may be formed using different materials. In some embodiments, the system lacks any structural ability to support body weight of an amputee. In some specific embodiments, the system is generally unrelated to the structural properties of a prosthesis, for example, to support movement, positioning, or load.

In some embodiments, the substrate may include one or more sensors in communication with the residual limb and configured to receive one or more parameters associated with substrate, the residual limb, or a combination thereof. For example, the sensors may include a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof. Additionally or alternatively, the stretch sensor may include a piezo resistive sensor, the movement sensor may include an accelerometer, a gyroscope, an optical sensor, a hall effect sensor, or a resistive flexion sensor, the oxygen sensor may include an optical oximeter, the pressure sensor may include a capacitive sensor, a force sensing resistor, an optical sensor, a pneumatic sensor, a strain-gauge sensor, a piezoelectric sensor, or a piezo chromic sensor, and the vibrational sensor may include an accelerometer or a gyroscope.

In some embodiments, the sensors may obtain (e.g., measure, read) a respective reading from the amputee and may communicate the reading (e.g., via the conductive traces) to a device that is coupled with the interconnect or otherwise in communication (e.g., wireless communication) with the substrate. In some embodiments, the sensors may provide the readings to the device (e.g., via the interconnect or via wireless communication) using one or more dedicated feedback paths within the substrate. The feedback paths may be wires or conductive traces different than the conductive traces for activating the electrodes. The wireless connection may include a Wi-Fi or Bluetooth connection.

In some embodiments, the substrate may include or otherwise be in communication with a second controller configured to cause one or more electrodes to transmit electrical current to the residual limb. The controller may be configured to selectively activate one or more electrodes. For example, the controller may transmit the electrical current through the residual limb using one or more electrodes that are selectively determined. In other examples, electrodes for transmitting electrical current through a residual limb of the amputee may be selected by an artificial intelligence algorithm.

In some embodiments, the substrate may be configured to contact a user's skin. The substrate may be configured to transmit an electrical current through the user's skin using one or more electrodes (e.g., an array of electrodes). The electrodes may be coupled with an interconnect (e.g., a silicone interconnect, a rigid silicone interconnect) via a conductive material, such as respective conductive traces. In some embodiments, the conductive traces may include a conductive ink that is configured to communicate signaling (e.g., from a controller or source external to the silicone substrate) that activates (e.g., engages, turns on) one or more of the electrodes. The electrodes, when activated, may stimulate nerve fibers in the user's skin.

In some embodiments, the substrate may include one or more layers. For example, the electrodes may be embedded within a second layer and a first layer may be formed over the top (e.g., above, in contact with) the second layer. Thus, the electrodes may be generally coplanar or otherwise aligned with an upper surface of the second material, but may be recessed relative to an upper surface of the first material. The first material and the second material may be made of the same material (e.g., a same silicone material) or a different material (e.g., a different silicone material). In some embodiments, the total thickness of the substrate (e.g., of the first layer and the second layer) may be between 0.1 mm and 26 mm.

In some embodiments, the electrodes may be adapted to the conductive traces. That is, the electrodes may be in contact and electrically coupled (e.g., directly coupled) with the conductive traces (e.g., the conductive ink) such that they are configured to receive signaling. In some instances, the conductive ink may be configured to communicate signaling to each electrode from the interconnect and to communicate signaling to the interconnect from each electrode. The conductive traces may communicate signaling to and from the interconnect, which may be configured as a pin connection and/or may include a plurality of crimps for coupling with the conductive ink. For example, a pin connection may be configured to communicate signaling (e.g., via the pins) to a device connected to the pins. In other examples, the interconnect may be coupled with the conductive traces by crimping (e.g., crimping down) to a region where the conductive traces terminate, thus forming an electrical connection between the traces and the interconnect.

Additionally or alternatively, the substrate may be stretchable. For example, the substrate may be stretched in any direction. When stretched, the conductive ink may communicate signaling to each electrode from the interconnect and communicate signaling to the interconnect from each electrode despite the substrate being stretched.

In some embodiments, the conductive ink may include various conductive materials, (e.g., silver infused nanoparticles, gold infused nanoparticles, a silver coated material, a conductive carbon material, or a combination thereof).

In some embodiments, the substrate may include conductive topical products (e.g., conductive hydrogel, topical creams, etc.) for electrode attachment and conductivity with the user's skin. In other embodiments, the substrate may include (e.g., in addition to or in place of the conductive hydrogel) a cooling material, a moisture wicking material, an antimicrobial material, an antibacterial material or a combination thereof.

In some embodiments, the substrate may include or otherwise be in communication with a second controller configured to cause one or more electrodes to stimulate nerve fibers in the user's skin (e.g., using electrical current). The controller may be configured to selectively activate one or more electrodes. For example, the controller may transmit the electrical current through the user's skin using one or more electrodes that are selectively determined. In other examples, electrodes for stimulating nerve fibers in the user's skin may be selected by an artificial intelligence algorithm.

In some embodiments, the second controller may cause one or more of the electrodes to stimulate nerve fibers in the user's skin using one or more sensations. For example, the electrodes may simulate a tapping sensation, a kneading sensation, a rolling sensation, a cupping sensation, a scraping sensation, or a combination thereof. In some embodiments, a location of the tapping sensation, the kneading sensation, the rolling sensation, the cupping sensation, or the scraping sensation is selectively determined by the user (e.g., via the second controller) or using an artificial intelligence algorithm. Additionally or alternatively, the second controller may be associated with a graphical user interface (GUI) configured to receive a user input for selecting the tapping sensation, the kneading sensation, the rolling sensation, the cupping sensation, or the scraping sensation.

In some embodiments, the substrate may include a power source. That is, the substrate may include its own power source such that it does not rely or otherwise need a wired power connection. In some embodiments, the power source may be coupled with the rigid interconnect and configured to power the plurality of embedded electrodes and the electrode controller.

In some embodiments, the substrate and liner may be operated by a user. For example, the liner may be configured to attach to the residual limb of an amputee (e.g., the user) such that its electrodes are in electrical communication with the residual limb. The substrate may be configured to transmit (e.g., via an electrode controller) electrical current through the residual limb. In some embodiments, the electrode controller may be in communication with each electrode via an interconnect and one or more conductive traces (e.g., traces formed of conductive ink). When the electrodes are activated, they may stimulate nerve fibers in the residual limb.

In some embodiments, the substrate may be in communication with a second controller. The second controller may transmit signaling to the substrate indicating to transmit the electrical current through the residual limb using one or more electrodes. The signaling may allow for the electrical current to be transmitted through the residual limb for a duration (e.g., a predefined duration or until different signaling is received). That is, the nerve fibers in the residual limb may be stimulated for a duration indicated by the signaling received from the second controller.

In some embodiments, the nerve fibers in the residual limb may be stimulated using a tapping sensation, a kneading sensation, a rolling sensation, a cupping sensation, a scraping sensation, or a combination thereof indicated by the signaling received from the second controller. In some instances, the second controller may transmit additional (e.g., updated, different) signaling indicating to stop the stimulation or to switch a type of sensation used to stimulate the nerve fibers in the residual limb. For example, the signaling may indicate switching from one type of stimulation to another (e.g., a different) type of stimulation.

In some embodiments, the signaling transmitted from the second controller may indicate a stimulation intensity for stimulating nerve fibers in the residual limb. Additionally or alternatively, the signaling may indicate a pulse intensity for stimulating nerve fibers in the residual limb.

The substrate may include one or more sensors. For example, the substrate may include sensors for gathering physiological data from the user (e.g., via the user's residual limb). The electrode controller may receive the physiological data from the user and may transmit signaling (e.g., second signaling) to the second controller indicating the physiological data. In some embodiments, the second signaling may be transmitted such that the physiological data is displayed at a graphical user interface (GUI) of a device associated with the second controller.

The substrate may include a controller (e.g., an electrode controller or a sensor controller) configured to transmit signaling (e.g., third data) associated with data received from the sensors. The signaling may be associated with data received from a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof.

In some embodiments, the substrate may include one or more additional sensors (e.g., second sensors). The substrate may include a controller (e.g., an electrode controller or a sensor controller) configured to transmit signaling (e.g., fourth data) associated with data received from the second sensor. The signaling may be associated with data associated with a skin temperature, a respiration rate, a heart rate, a heart rate variability (HRV), a galvanic skin response, a pulse oxygen reading, a blood oxygen saturation, a blood sugar level, or a combination thereof.

In some embodiments, the substrate may include one or more additional sensors (e.g., third sensors). The substrate may include a controller (e.g., an electrode controller or a sensor controller) configured to transmit signaling (e.g., fifth data) associated with data received from the third sensor. The signaling may be associated with data associated with a mechanical strain of the liner.

In some instances, based on the data gathered from one or more sensors (e.g., sensors, second sensors, third sensors), the electrical current used to stimulate the nerve fibers of the residual limb may be adjusted.

In some embodiments, the signaling may be transmitted (e.g., to the second controller) using a Wi-Fi or Bluetooth connection.

A user may engage with the substrate by positioning his or her residual limb proximate to the substrate such that the plurality of electrodes are in electrical communication with the residual limb. A subset (or all) of the plurality of electrodes may then stimulate the nerve fibers in the residual limb. In some embodiments, muscles in the residual limb may be stimulated responsive to transmitting electrical current with the plurality of electrodes.

In some embodiments, the electrodes may be activated based on a combination of pins of the interconnect that are driven to a first value. The pins may be driven by a physical connection to the interconnect. In other embodiments, the conductive traces may be driven by a controller (e.g., an electrode controller) that is in wireless communication with an external device (e.g., a user device, a second controller). Additionally or alternatively, the electrodes may be activated based on an analog or a digital switch (e.g., H-Bridge circuit) coupled with the conductive ink via an interconnect. In other embodiments, the interconnect may be configured to receive signaling from an external device and transmit signaling to the external device (e.g., a user device, a second controller). In some embodiments, the substrate may be operated by a user. For example, the substrate may be configured to attach to a user's skin such that its electrodes are in electrical communication with the user's skin. The substrate may be configured to transmit (e.g., via an electrode controller) electrical current through the user's skin. In some embodiments, the electrode controller may be in communication with each electrode via an interconnect and one or more conductive traces (e.g., traces formed of conductive ink). When the electrodes are activated, they may stimulate nerve fibers in the user's skin.

In some embodiments, the substrate may be in communication with a second controller. The second controller may transmit signaling to the substrate indicating to transmit the electrical current through the user's skin using one or more electrodes. The signaling may allow for the electrical current to be transmitted through the user's skin for a duration (e.g., a predefined duration or until different signaling is received).

That is, the nerve fibers in the user's skin may be stimulated for a duration indicated by the signaling received from the second controller.

In some embodiments, the nerve fibers in the user's skin may be stimulated using a tapping sensation, a kneading sensation, a rolling sensation, a cupping sensation, a scraping sensation, or a combination thereof indicated by the signaling received from the second controller. In some instances, the second controller may transmit additional (e.g., updated, different) signaling indicating to stop the stimulation or to switch a type of sensation used to stimulate the nerve fibers in the user's skin. For example, the signaling may indicate switching from one type of stimulation to another (e.g., a different) type of stimulation.

In some embodiments, the signaling transmitted from the second controller may indicate a stimulation intensity for stimulating nerve fibers in the user's skin. Additionally or alternatively, the signaling may indicate a pulse intensity for stimulating nerve fibers in the user's skin.

The substrate may include one or more sensors for gathering physiological data from the user (e.g., via the user's skin). The electrode controller may receive the physiological data from the user and may transmit signaling (e.g., second signaling) to the second controller indicating the physiological data. In some embodiments, the second signaling may be transmitted such that the physiological data is displayed at a graphical user interface (GUI) of a device associated with the second controller.

In some embodiments, the substrate may include one or more sensors. The substrate may include a controller (e.g., an electrode controller or a sensor controller) configured to transmit signaling (e.g., third data) associated with data received from the sensors. The signaling may be associated with data received from a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof.

In some embodiments, the substrate may include one or more additional sensors (e.g., third sensors). The substrate may include a controller (e.g., an electrode controller or a sensor controller) configured to transmit signaling (e.g., fifth data) associated with data received from the third sensors. The signaling may be associated with data associated with a mechanical strain of the liner.

In some instances, based on the data gathered from one or more sensors (e.g., sensors, second sensors, third sensors), the electrical current used to stimulate the nerve fibers of the user's skin may be adjusted.

In some embodiments, the signaling may be transmitted (e.g., to the second controller) using a Wi-Fi or Bluetooth connection.

In some embodiments, a substrate may be manufactured. In some embodiments, the system may be manufactured with or without a liner. The substrate and liner may be manufactured by forming a first layer (e.g., a silicone layer, a polymer layer) that includes a plurality of electrodes (e.g., an array of electrodes). In the first layer, a first portion of an interconnect may be formed using a second material (e.g., a rigid silicone material). A plurality of conductive paths (e.g., conductive traces) may be formed between the electrodes and the first portion of the interconnect. In some embodiments, each electrode may be coupled with (e.g., adapted to) a respective conductive path. A second layer (e.g., a silicone layer, a polymer layer) may be formed over the first layer such that the electrodes are embedded relative to an upper surface of the second layer. A second portion of the interconnect may be formed in the second layer and a liner may be molded to (e.g., bonded with) the second layer. The substrate and liner assembly may operate as described herein.

In some embodiments, the first layer may be formed by depositing a first material (e.g., a polymer material) and placing (e.g., selectively placing) the electrodes in the first material. In other embodiments, the first layer may be formed by placing (e.g., selectively placing) the electrodes and depositing a first material (e.g., a polymer material) around the electrodes. The electrodes may be generally coplanar with or recessed relative to an upper surface of the first material. In some instances, the electrodes may be molded (e.g., using an injection molding process) in the first material. A vulcanization process may be performed on the first layer after the electrodes and the first material are placed.

In some embodiments, a third material (e.g., a silicone material) may be formed around one or more of the electrodes. The third material may be a non-conductive material and may serve as a barrier for each respective electrode.

In some embodiments, one or more apertures may be formed in the first material. A respective sensor may be formed (e.g., placed) in each aperture. The sensor(s) may include a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof. A conductive material (e.g., a wire, a trace, an electrical connection) may be formed between each sensor and the interconnect such that the conductive material acts as a feedback path for each respective sensor.

In some embodiments, the conductive paths may be formed using a conductive ink. The conductive paths may be formed by screen-printing the conductive ink between each electrode, such that the electrodes adapt to the respective conductive traces, and the first portion of the interconnect. After the conductive paths are screen-printed, they may be cured for a duration. In other embodiments, the conductive paths may be formed by a syringe-dispensing process, by dipping the first layer in a conductive material, spraying the first layer with a conductive material, or a combination thereof. In some embodiments, the conductive paths may include silver infused nanoparticles, gold infused nanoparticles, a silver coated material, a conductive carbon material, or a combination thereof.

In some embodiments, the substrate and the liner may be formed into a tubular shape by adhering a first portion of the substrate and liner to a second portion of the substrate and liner (e.g., via a seam). The substrate and/or the liner may include biocompatible materials and a thickness of the first layer (e.g., a silicone layer) and the second layer (e.g., a silicone layer) may be between 0.1 mm and 26 mm.

In some embodiments, the substrate described herein may include circuitry (e.g., a controller, a processor) or may otherwise be in electronic communication with a device including circuitry (e.g., a controller, a processor) configured to execute instructions that cause the substrate to perform various operations. In some embodiments, the circuitry may execute instructions that cause the substrate to transmit electrical current through a user's skin via a plurality of electrodes that are in electrical contact with the user's skin. The plurality of electrodes may be coupled with an interconnect via respective conductive ink traces. In some embodiments, the electrical current may be associated with a first sensation for stimulating the user's skin. The circuitry may be configured to transmit, to a switching matrix of the substrate, signaling indicating to transmit the electrical current through the user's skin, using the first sensation, via one or more of the plurality of electrodes. In some embodiments, a controller (e.g., an electrode controller) may receive the signaling and select a type of sensation to use when the electrical current is transmitted through the user's skin.

In some embodiments, the circuitry may be configured to execute instructions to store a minimum stimulus level for stimulating the user's skin. The minimum stimulus level may be stored to a user device associated with the substrate and may be a default setting for stimulating the user's skin. For example, a user may prefer a minimum intensity, a minimum speed, a type of stimulus, or a combination thereof. Such preferences may be stored to memory included in a controller (e.g., an electrode controller) such that, when the substrate is powered-on, the substrate may begin operating using the stored preferences.

In some embodiments, the circuitry may be configured to execute instructions to transmit electrical current through the user's skin, via the plurality of electrodes, using a second sensation for stimulating the user's skin that is different than the first sensation. The circuitry may be configured to transmit, to the switching matrix of the substrate, signaling indicating to switch transmitting the electrical current through the user's skin from using the first sensation to the second sensation via one or more of the plurality of electrodes. In some embodiments, a controller (e.g., an electrode controller) may receive the signaling and switch transmitting electrical current through the user's skin from using the first sensation to the second sensation via one or more of the plurality of electrodes.

In some embodiments, the first sensation may be associated with transmitting electrical current through the user's skin using a first subset of the plurality of electrodes, and the second sensation may be associated with transmitting electrical current through the user's skin using a second subset of the plurality of electrodes that is different than the first subset of the plurality of electrodes. In some embodiments, the first sensation may be associated with a tapping sensation, a kneading sensation, a rolling sensation, a cupping sensation, or a scraping sensation.

Additionally or alternatively, the first indication may indicate a duration to stimulate the user's skin via the plurality of electrodes. In some embodiments, the first sensation may be associated with a stimulation intensity for stimulating nerve fibers under the user's skin In some embodiments, the circuitry may execute instructions that cause the substrate to stop transmitting electrical current through the user's skin. The circuitry may be configured to transmit, to the switching matrix of the substrate, signaling indicating to refrain from transmitting electrical current through the user's skin.

In some embodiments, the user device in communication with the substrate may be a mobile device (e.g., a mobile phone), a computer, a wearable device, or any suitable electronic device. The user device may be in electronic communication with the substrate via a Wi-Fi or Bluetooth connection.

In some embodiments, the circuitry may be configured to receive physiological data from one or more sensors of the substrate. The circuitry may execute instructions to display, at a graphical user interface (GUI) of the user device, a representation of the physiological data from the one or more sensors of the substrate. In some embodiments, the representation of the physiological data may include a measurement of a distance that the substrate is stretched, a temperature of the substrate, a rate at which the substrate is moving, a direction that the substrate is moving, a moisture reading of the substrate, an oxygen reading of a user of the substrate, a pressure reading associated with the substrate, a bacteria reading associated with the substrate, a vibrational reading associated the substrate, a blood glucose level associated with a user of the substrate, a pulse oxygen level associated with a user of the substrate, a magnetic flux reading associated with the substrate, or a combination thereof.

In some embodiments, the circuitry may execute instructions that cause the substrate to adjust a pressure level of the substrate. The circuitry may be configured to transmit, to the switching matrix of the substrate, signaling indicating to adjust the pressure level of the substrate. In some embodiments, the substrate may include one or more additional components (e.g., pumps, fans, etc.) that are configured to adjust the pressure level of the substrate.

In some embodiments, the circuitry may receive signaling associated with a mechanical strain of a liner of the substrate. In response to receiving the signaling, the circuitry may transmit signaling to adjust the electrical current through the user's skin.

In some embodiments, the circuitry may execute instructions to perform one or more operations based on signaling received from an artificial intelligence algorithm stored to the user device.

Various aspects of this disclosure relate to a method of using a system described anywhere in this disclosure.

FIG. 1 depicts a system 100, which comprises a prosthetic liner 101 bonded to a substrate 110. The substrate 110 comprises an embedded array of electrodes 102 (shown in FIG. 2). The prosthetic liner 101 and substrate 110 may collectively receive a residual limb (not shown) such that the liner 101 fits underneath a region of a prosthesis 103 (shown in FIG. 2) that also receives the residual limb and provides suspension, protection and cushion to a residual limb of an amputee.

Each electrode 102 of the array of electrodes 102 in the substrate 110 is in electrical communication with an electrode controller 104, which electrical communication is mediated by conductive ink 154 formed in the substrate 110. In some embodiments, the electrical communication can be mediated by conductors other than conductive ink 154, such as any type of conductive material.

The prosthetic liner 101 and/or substrate 110 may comprise a tube comprising a wall, an edge that defines a terminus of the wall, an open end bounded by the edge, and a void space defined by the wall, wherein the void space configured to receive the residual limb through the open end. In some specific embodiments, the tube comprises a closed end that is continuous with the wall, for example, such that the void space is defined by the closed end, the wall, and the open end.

In some embodiments, the prosthetic liner 101 and/or substrate 110 generally comprises a concave interior surface of the tube and a convex exterior surface of the tube, wherein the edge defines a boundary between the concave interior surface and the convex exterior surface. As described herein, the substrate 110 may be formed as a generally flat, flexible surface. During one or more manufacturing processes, the substrate 110 may be formed into a tubular shape by connecting two or more edges together (e.g., via a seam).

FIG. 1 depicts an interconnect 150 that is coupled with the conductive ink 154. In some embodiments, the interconnect 150 may include a pin connection for coupling with an external source. The interconnect may be molded to the substrate 110 or may be connected (e.g., after the substrate 110 is formed) using one or more crimps, pins, or other attachment means (not shown). In some examples, the interconnect 150 may be an external interconnect configured to connect with the substrate via one or more channels in the substrate 101 as described with reference to FIGS. 13 through 14b.

The electrodes 102 included in the substrate 110 may include an anterior-lateral-proximal electrode, an anterior-lateral-distal electrode, a posterior-lateral-distal electrode, and a posterior-lateral-proximal electrode. In some embodiments, the substrate 110 may include any quantity of electrodes 102. In some embodiments, the electrodes 102 included in the substrate 110 may include any quantity of electrodes 102. In the illustrated embodiment, there are eight electrodes 102. The electrodes of 102 may be placed in any position within the substrate 110, such as the position of electrodes 102a and 102b, for example.

The sensors 107 (shown in FIG. 3) included in the substrate 110 may include an anterior-lateral-proximal sensor, an anterior-lateral-distal sensor, a posterior-lateral-distal sensor, and a posterior-lateral-proximal sensor. In some embodiments, the substrate 110 may include any quantity of sensors 107. By placing at least one sensor 107 relative to the top of the substrate 110 and another sensor 107 relative to the bottom of the substrate 110, blood flow patterns of the residual limb or user's skin may be monitored. For example, the configuration may allow for the detection of restricted flow at the distal end of the limb by analyzing the differences in readings between the sensors 107.

By way of example, in some embodiments, sensors 107a and 107b may be photoplethysmography (PPG) sensors. In such embodiments, by placing one PPG sensor towards the top of the substrate 110 and another PPG sensor towards the bottom of the substrate 110, blood flow patterns can be effectively monitored and compared. Furthermore, in such embodiments, the placement, monitoring, and comparison of PPG sensors can be used to detect restricted blood flow to the distal end of the limb by analyzing the differences in readings between the top and bottom sensors. To be clear, there may be any number of PPG sensors, and they may be placed anywhere throughout the substrate.

FIG. 1 also depicts an electrode controller 104 (e.g., circuit board assembly 130), which may be associated with or otherwise be referred to as an electrode controller 104. The circuit board assembly 130 may include a battery 131 in electrical communication with the printed circuit board assembly 130. When the electrode controller 104 is in electrical communication with the embedded wires or the conductive ink 154, then a microprocessor (not shown) of the printed circuit board assembly 130 of the electrode controller 104 controls the transmission of electrical current between the battery 131 and the embedded wires or conductive ink 154 to control whether an electrode of the array of electrodes will transmit electrical current, which the electrode receives from the battery 131, and whether an electrode of the array of electrodes will receive electrical current, which the electrode transmits to the battery 131.

Figure 2:
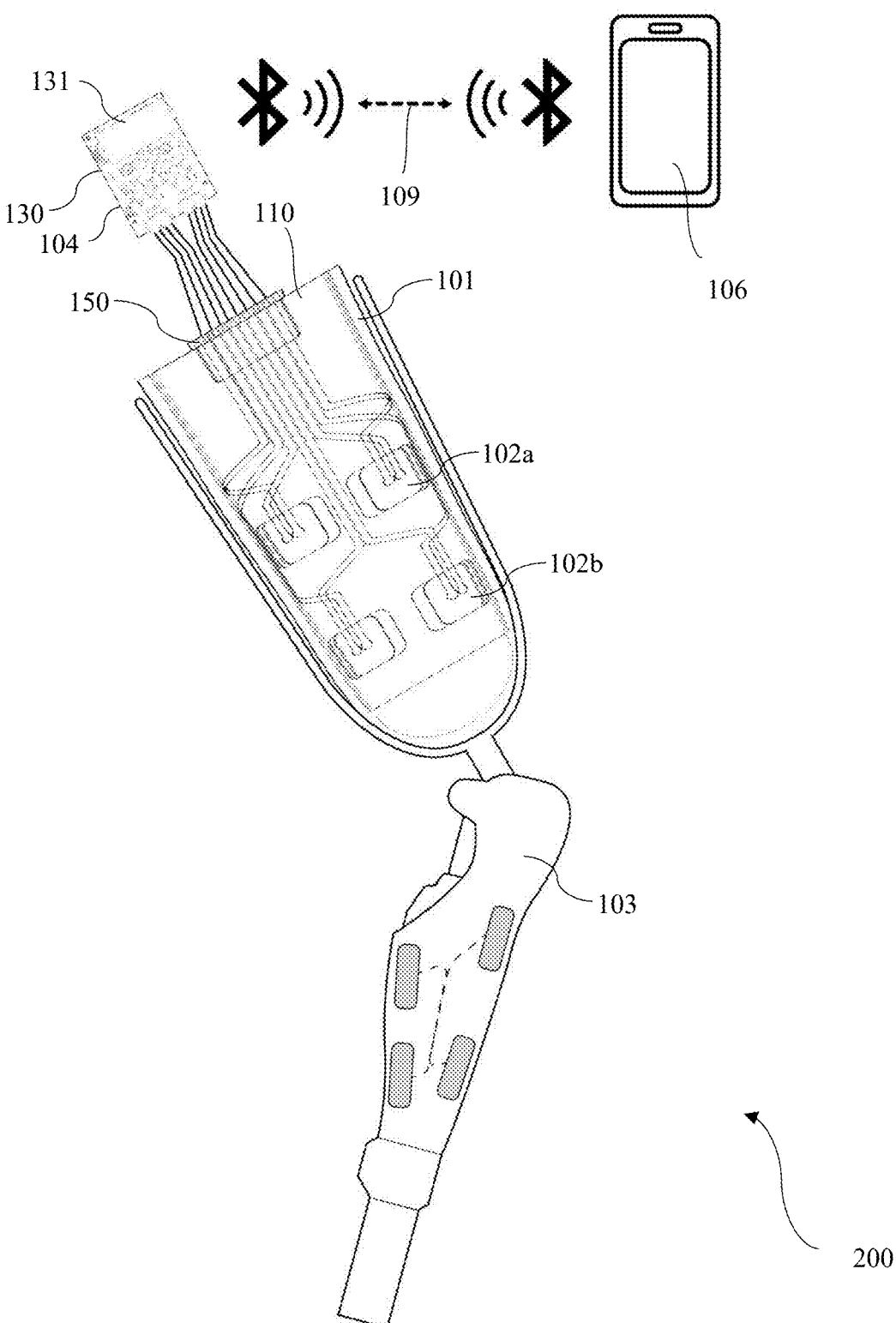

FIG. 2 depicts a system 200, which comprises a substrate 110 that includes an embedded array of electrodes 102. The substrate 110 may collectively receive a residual limb (not shown) such that the substrate 110 fits underneath a region of a prosthesis 103 that also receives the residual limb.

FIG. 2 depicts a wireless, Bluetooth-mediated interface 109 between the electrode controller 104 (e.g., the circuit board assembly 130) and a second controller 106 (e.g., of an external device). The wireless, Bluetooth-mediated interface 109 between the electrode controller 104 and the second controller 106 allows amputees to contact the sensors 107 to activate electrodes 102 of the array of electrodes 102 to stimulate their residual limbs even when an amputee is not wearing the prosthetic 103 and substrate 110, for example, such as when the amputee has removed the prosthetic 103 to sleep. In other embodiments, the system 100 lacks a second controller 106, and sensors 107 are connected directly to the electrode controller 104. That is, the system 100 may lack a Bluetooth-mediated interface 109. It should be appreciated that the Bluetooth-mediated interface 109 may be supplemented or replaced with any other suitable communication medium between the electrode controller 104 and the second controller 106 (e.g., WiFi, BlueTooth Low Energy, Zigbee, Z-Wave, 6LoWPAN, etc.). In some embodiments, the second controller 106 may be connected directly (e.g., hardwired) to the electrode controller 103.

In some embodiments, the sensors may be located in a prosthetic cover used on a prosthetic limb in combination with the substrate system.

Each sensor may be configured to sense at least one modality (e.g., one or both of force and pressure). Each sensor may be, for example, a force sensing resistor. In some embodiments, each sensor comprises a resistor that is configured to sense at least one modality (e.g., one or both of force and pressure).

In some embodiments, the system is configured such that the amplitude of the electrical current transmitted and received by electrodes through the residual limb directly correlates with a modality (e.g., pressure or force) sensed by a sensor, for example, such that increased modality (e.g., increased pressure or increased force) correlates with increased amplitude.

In some embodiments, the electrodes are in communication with the sensors such that two or more electrodes are activated in response to sensing by one or more sensors. In some specific embodiments, the electrodes are in communication with the sensors such that two electrodes are activated in response to sensing by one sensor.

In some embodiments, each sensor corresponds to at least two electrodes. In some specific embodiments, each sensor corresponds to two electrodes. In some embodiments, each electrode corresponds to at least one sensor. In some specific embodiments, each electrode corresponds to at least two sensors.

A sensor corresponds to an electrode if the sensor is in communication with the electrode such that the electrode will transmit or receive electrical current to or from the residual limb when both the sensor senses a modality (e.g., force or pressure) and the electrode is in electrical communication with the residual limb.

An electrode corresponds to a sensor if the sensor is in communication with the electrode such that the electrode will transmit or receive electrical current to or from the residual limb when both the sensor senses a modality (e.g., force or pressure) and the electrode is in electrical communication with the residual limb.

In some embodiments, the system comprises a secondary controller in wireless communication with the electrodes such that the secondary controller can bypass the sensors to cause each electrode of the array of electrodes to transmit or receive electrical current to or from the residual limb when the array of electrodes is in electrical communication with the residual limb.

In some embodiments, the system 200 may lack sensors 107 and a second controller 106 entirely. In such embodiments, the electrodes 102 may be activated by a user on an electrode controller 104 directly (e.g., by a power switch or by any suitable user interface).

In some embodiments, the second controller 106 may transmit signaling to the electrode controller 104, which may cause one or more of the electrodes 102 to stimulate nerve fibers in the user's skin (or the residual limb) using one or more touch modalities or sensations. For example, the electrodes 102 may simulate a tapping sensation, a kneading sensation, a rolling sensation, a cupping sensation, a scraping sensation, or a combination thereof. In some embodiments, a location of the tapping sensation, the kneading sensation, the rolling sensation, the cupping sensation, or the scraping sensation is selectively determined by the user (e.g., via the second controller 106) or using an artificial intelligence algorithm that utilizes a machine learning model. In some embodiments, the machine learning model may be trained based on feedback from a user of the substrate 110. For example, in some embodiments, a user may submit pain feedback to the secondary controller 106 (e.g., in the form of a Visual Analog Scale), and that feedback may be used to help improve a machine learning model. However, it should be appreciated that such user feedback may still be implemented in non-machine learning applications (such as utilizing algorithms or memory settings to determine which settings the user prefers).

As to some examples of types of machine learning and/or machine learning models that may be implemented for one or more purposes, consider one or more of a support vector machine (SVM) model, a k-nearest neighbors (KNN) model, an ensemble classifier model, a neural network (NN) model, etc. As an example, a machine learning model can be a deep learning model (e.g., deep Boltzmann machine, deep belief network, convolutional neural network, stacked auto-encoder, etc.), an ensemble model (e.g., random forest, gradient boosting machine, bootstrapped aggregation, AdaBoost, stacked generalization, gradient boosted regression tree, etc.), a neural network model (e.g., radial basis function network, perceptron, back-propagation, Hopfield network, etc.), a regularization model (e.g., ridge regression, least absolute shrinkage and selection operator, elastic net, least angle regression), a rule system model (e.g., cubist, one rule, zero rule, repeated incremental pruning to produce error reduction), a regression model (e.g., linear regression, ordinary least squares regression, stepwise regression, multivariate adaptive regression splines, locally estimated scatterplot smoothing, logistic regression, etc.), a Bayesian model (e.g., naive Bayes, average on-dependence estimators, Bayesian belief network, Gaussian naive Bayes, multinomial naive Bayes, Bayesian network), a decision tree model (e.g., classification and regression tree, iterative dichotomiser 3, C4.5, C5.0, chi-squared automatic interaction detection, decision stump, conditional decision tree, M5), a dimensionality reduction model (e.g., principal component analysis, partial least squares regression, Sammon mapping, multidimensional scaling, projection pursuit, principal component regression, partial least squares discriminant analysis, mixture discriminant analysis, quadratic discriminant analysis, regularized discriminant analysis, flexible discriminant analysis, linear discriminant analysis, etc.), an instance model (e.g., k-nearest neighbor, learning vector quantization, self-organizing map, locally weighted learning, etc.), a clustering model (e.g., k-means, k-medians, expectation maximization, hierarchical clustering, etc.), etc.

Additionally or alternatively, the second controller 106 may be associated with a graphical user interface (GUI) configured to receive a user input for selecting the touch modalities and sensations, including tapping sensation, the kneading sensation, the rolling sensation, the cupping sensation, or the scraping sensation.

Figure 3:
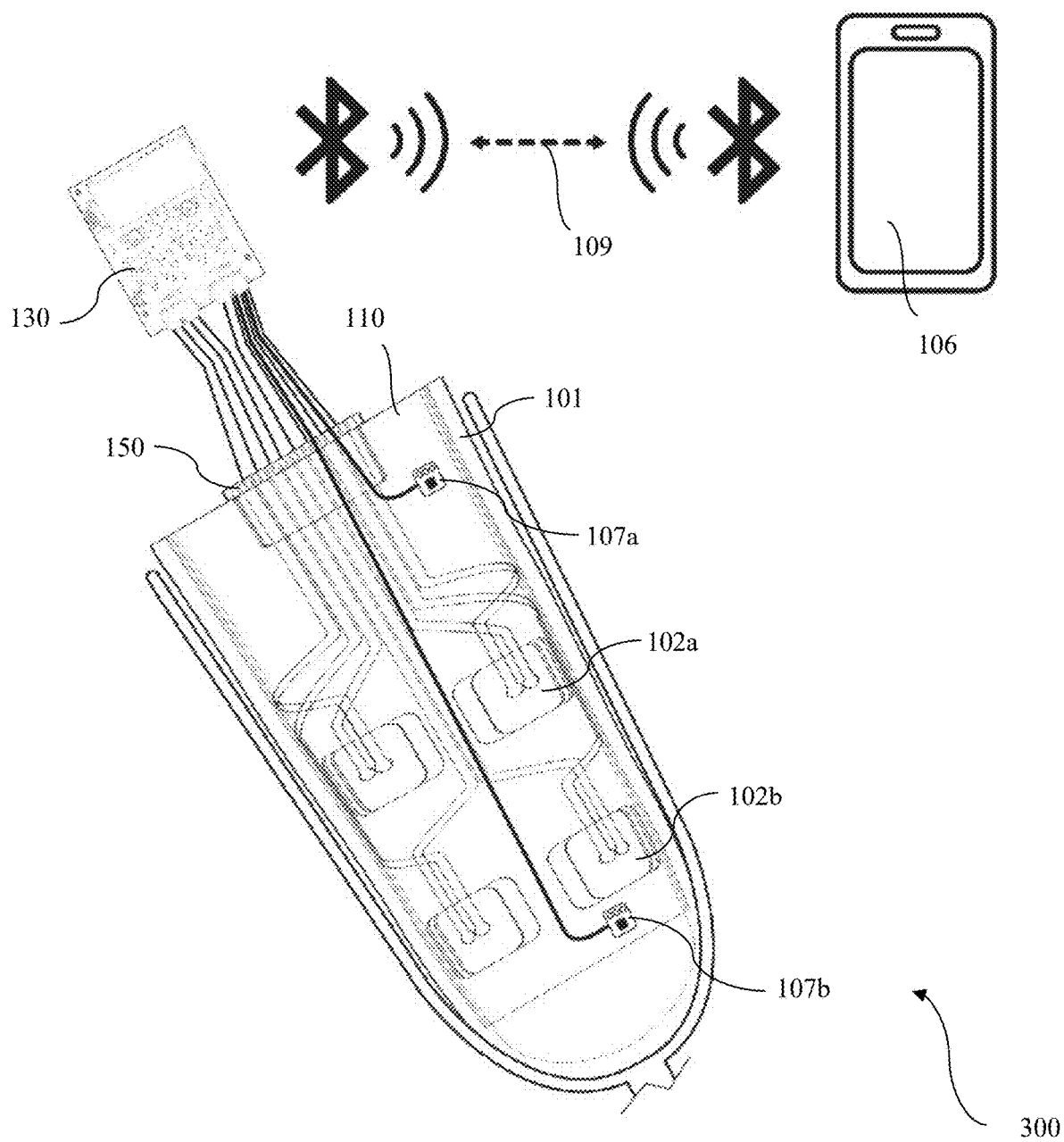
FIG. 3 depicts a wireless, Bluetooth-mediated interface that supports nerve modulation as described herein.

FIG. 3 depicts a wireless, Bluetooth-mediated interface 109 between the electrode controller 104 (e.g., the circuit board assembly 130) and a second controller 106 (e.g., of an external device). The wireless, Bluetooth-mediated interface 109 between the electrode controller 104 and the second controller 106 allows amputees to contact the sensors 107, which may provide one or more readings to the external device. In other embodiments, the system 300 lacks a second controller 106, and sensors 107 are connected directly to the electrode controller 104. That is, the system may lack a Bluetooth-mediated interface 109.

In some embodiments, the second controller 106 may transmit signaling to the electrode controller 104, which may cause one or more of the sensors 107 to activate. In some embodiments, the substrate 110 may include a sensor 107 at any location on the substrate 110. Moreover, the substrate 110 may include any quantity of sensors. As described herein, the sensors 107 may include any one or more of a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, and/or a magnetic flux sensor. Additionally or alternatively, the stretch sensor may include a piezo resistive sensor, the movement sensor may include an accelerometer, a gyroscope, an optical sensor, a hall effect sensor, or a resistive flexion sensor, the oxygen sensor may include an optical oximeter, the pressure sensor may include a capacitive sensor, a force sensing resistor, an optical sensor, a pneumatic sensor, a strain-gauge sensor, a piezoelectric sensor, or a piezo chromic sensor, and the vibrational sensor may include an accelerometer or a gyroscope. In some embodiments, the second controller 106 may be associated with a graphical user interface (GUI) configured to receive a user input or otherwise display data associated with the sensors 107.

Figure 4:
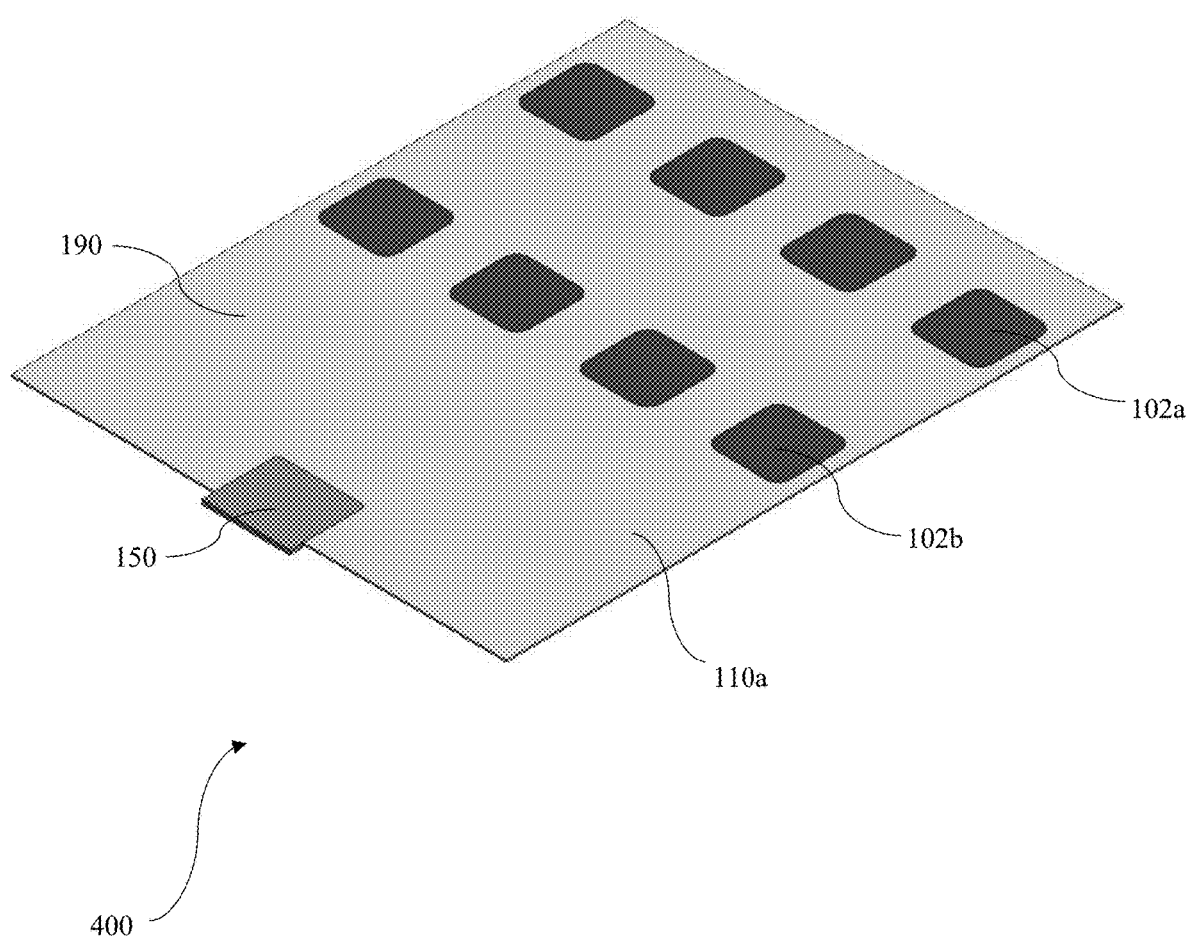
FIGS. 4 through 7 depict methods of manufacturing a substrate that supports nerve modulation as described herein.

FIG. 4 depicts a portion of a method 400 for manufacturing a substrate 110. In some embodiments, the substrate 110 may be formed from a material (e.g., a silicone material), thus may be referred as a silicone substrate 110, for purposes of this example. The substrate 110 may be formed of any suitable materials or polymer for biocompatibility and comfortability for a user, and compatibility between any other materials (e.g., polymers) used in the method of manufacturing 400 of a substrate 110. FIG. 4 depicts a first manufacturing step, where electrodes 102 are embedded within a first layer 110a. The substrate 110, when formed, may be bonded with a liner or may exist independent of a liner. If bonded with a liner 101, the substrate 110 may collectively receive a residual limb (not shown) such that the substrate 110 may be in direct contact with a user's skin.

A base layer (e.g., a first layer 110a) can be formed with an array of electrodes 102. The array may consist of any number of electrodes 102, e.g., two, four, six, eight, ten, etc. The electrodes 102 can be made of a conductive silicone material, or any other suitable electrode material. In some embodiments, the electrodes can be die cut from a sheet of a suitable conductive material, such as a sheet of conductive silicone, or injection molded onto (into) the first layer 110a. The electrodes 102 in the first layer 110a may be strategically recessed to accommodate for conductive topicals or gel pads to be inserted, may be non-protruding (or essentially "level" with, coplanar with an upper surface of the first layer 110a), or may be protruding to promote contact.

Further, within the first layer 110a, non-conductive silicone, or any other suitable base layer material 190, can be injected and molded around the array of electrodes 102 to bond the materials without the use of an adhesive. In some embodiments, the base layer material 190 may be a polymeric material. In some embodiments, the base layer material 190 may be a soft silicone of 5 mm or less. The base layer material 190 can be of a softness graded anywhere on the durometer shore hardness scale (e.g., Shore 5A or less) that promotes an embodiment's desired characteristics (e.g., comfortability).

In some embodiments, the forming of the first layer 110a will involve a vulcanization process. The vulcanization process can improve elasticity, tear strength, resistance to organic solvents, and abrasion, among other potential benefits. In some embodiments of this method, the base layer material 190 and the array of electrodes 102 are biocompatible to improve a substrate's 110 ability to perform an intended function, without eliciting any undesirable local or systemic effects in the user of the substrate 110.

In some embodiments, a bottom half of an interconnect 150 can be formed in the first layer 110a. This interconnect 150 can be made of rigid silicone, or any other suitable material. The bottom half of the interconnect 150 can be placed at the same time as the array of electrodes 102, so that the bottom half of the interconnect 150 is similarly bonded when the base layer material 190 is applied and molded.

In some embodiments, sensors (not shown) may be formed in the first layer 110a. Depending on the type of sensor, apertures (not shown) may be formed to allow for the sensor to interact with the signal the sensor is meant to transduce. For example, a diaphragm-based pressure sensor may be placed in an aperture of the first layer 110a to allow acoustic pressure signals to reach the diaphragm and be converted into sensor data. The sensors may be placed at the same time as the array of electrodes.

If sensors are included in an embodiment of a substrate 110, a feedback path (not shown) for the sensor signals may be incorporated. The feedback path may be made of a conductor capable of transmitting sensor data, such as a wire or a conductive path as described in the present disclosure. In some embodiments, the sensor may communicate wirelessly with other electronics, such as via Bluetooth, if the sensor includes the required circuitry (e.g., a communication module).

In some embodiments, the substrate 110 (e.g., the first layer 110a) may include one or more sensors in communication with the residual limb and configured to receive one or more parameters associated with silicone substrate, the residual limb, or a combination thereof. For example, the sensors may include a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof. Additionally or alternatively, the stretch sensor may include a piezo resistive sensor, the movement sensor may include an accelerometer, a gyroscope, an optical sensor, a hall effect sensor, or a resistive flexion sensor, the oxygen sensor may include an optical oximeter, the pressure sensor may include a capacitive sensor, a force sensing resistor, an optical sensor, a pneumatic sensor, a strain-gauge sensor, a piezo-electric sensor, or a piezo chromic sensor, and the vibrational sensor may include an accelerometer or a gyroscope.

Figure 5:
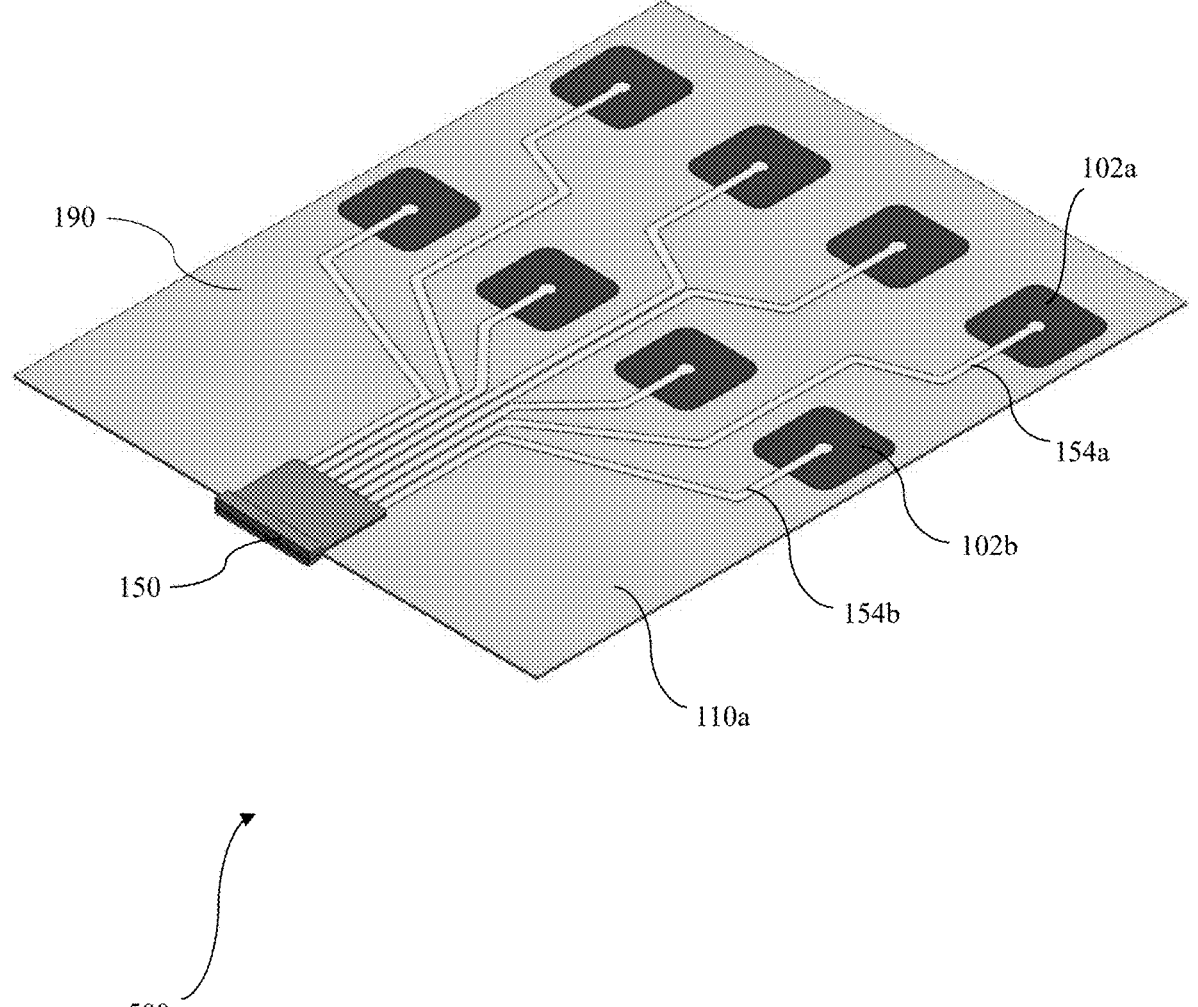

FIG. 5 depicts a portion of a method 500 for manufacturing a substrate 110. In some embodiments, the substrate 110 may be formed from a polymer material, thus may be referred as a silicone substrate 110, by way of example. FIG. 5 depicts a second manufacturing step, where conductive ink 154 is formed at the first layer 110a.

A screen-printed layer of conductive ink 154 may be formed on the first layer 110a. In the screen-printed layer, a conductive path may be formed between the array of electrodes 102 in the first layer 110a and the interconnect 150. The conductive path may touch directly to the electrodes 102, without requiring a connector. In some embodiments, the conductive path may be formed with flexible conductive silicone ink 154 via screen printing. In some embodiments, the screen-printed layer will be heat cured for approximately one hour at approximately 300 degrees Fahrenheit.

The conductive ink 154 may be applied in the screen-printed layer by other methods than screen printing, such as syringe dispensing, dipping, spraying, etc. In some embodiments, the conductive path will be formed with conductive wire, paint, or any other suitable method to form a conductive path between the electrodes 102 and the interconnect 150.

Figure 6:
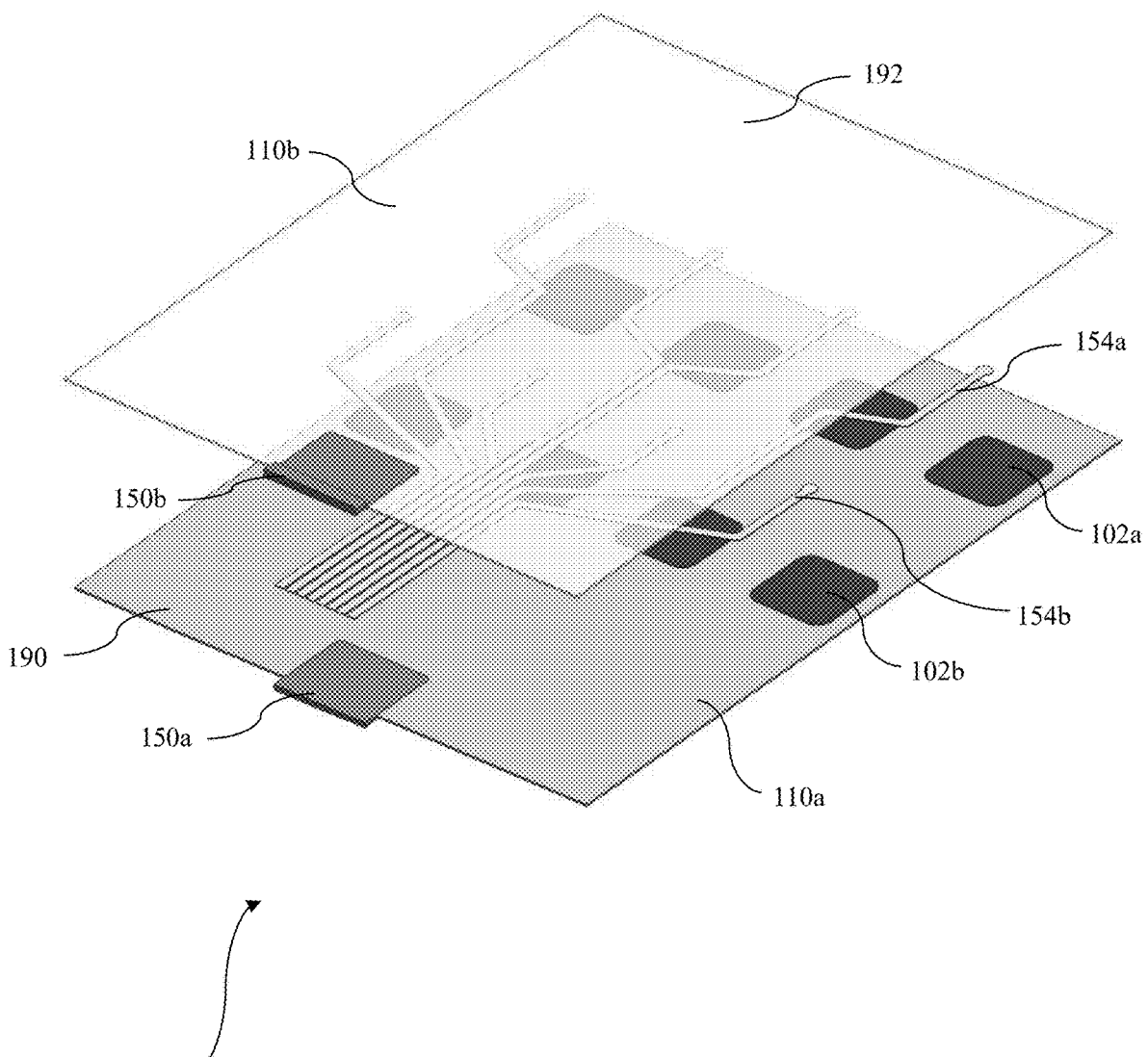

FIG. 6 depicts a portion of a method 600 for manufacturing a substrate 110. In some embodiments, the substrate 110 may be formed from a material (e.g., a silicone material), thus may be referred as a silicone substrate 110, although it should be appreciated that the substrate may be formed of any suitable material (e.g., polymeric material). FIG. 6 depicts a third manufacturing step, where a second layer 110b is formed over the conductive ink 154 and the first layer 110a.

A second layer 110b may include a top layer material 192 of the same or different material as the base layer material 190 of the first layer 110a, and can be formed over the screen-printed layer. In some embodiments, a top half of the interconnect 150 can be formed in the second layer 110b. The top half of the interconnect 150 may be formed of the same material or a different material as the bottom half, such as with a rigid silicone. Once the interconnect 150 is formed, it can be used to attach or provide connections for controllers, power sources, and connectivity to other systems, phones, wearables, etc.

Figure 7:
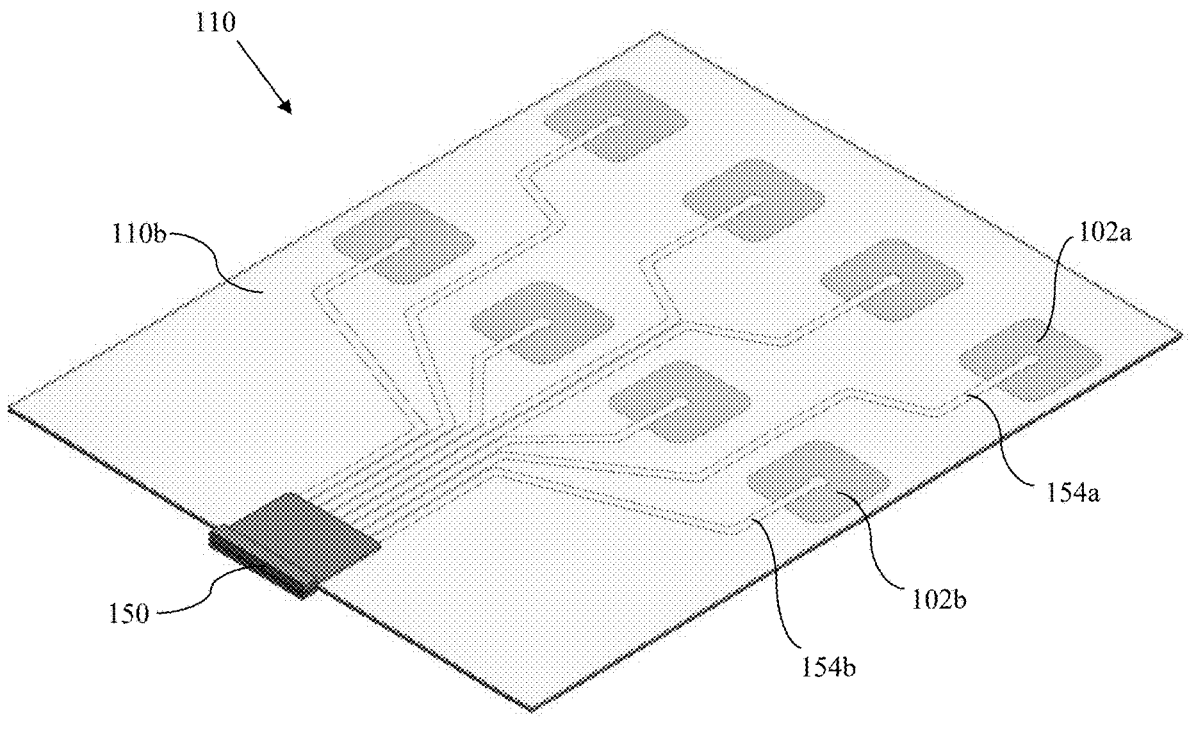
Figure 7:
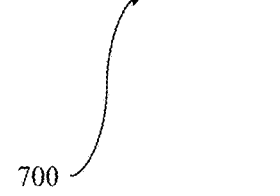

FIG. 7 depicts a completed embodiment of a method 700 for manufacturing a substrate 110 after the second layer 110b is formed over the conductive ink 154 and the first layer 110a. In other embodiments (not shown), the substrate 110 may be formed into a tubular shape by connecting two or more edges together via a seam. Additionally or alternatively, the substrate 110 may be bonded with a liner 101. A second layer 110b may serve as a protective barrier for the electrodes and the conductive ink. In some embodiments with a liner, the second layer 110b may serve as a protective barrier between the liner, and the electrodes and the conductive ink.

Figure 8:
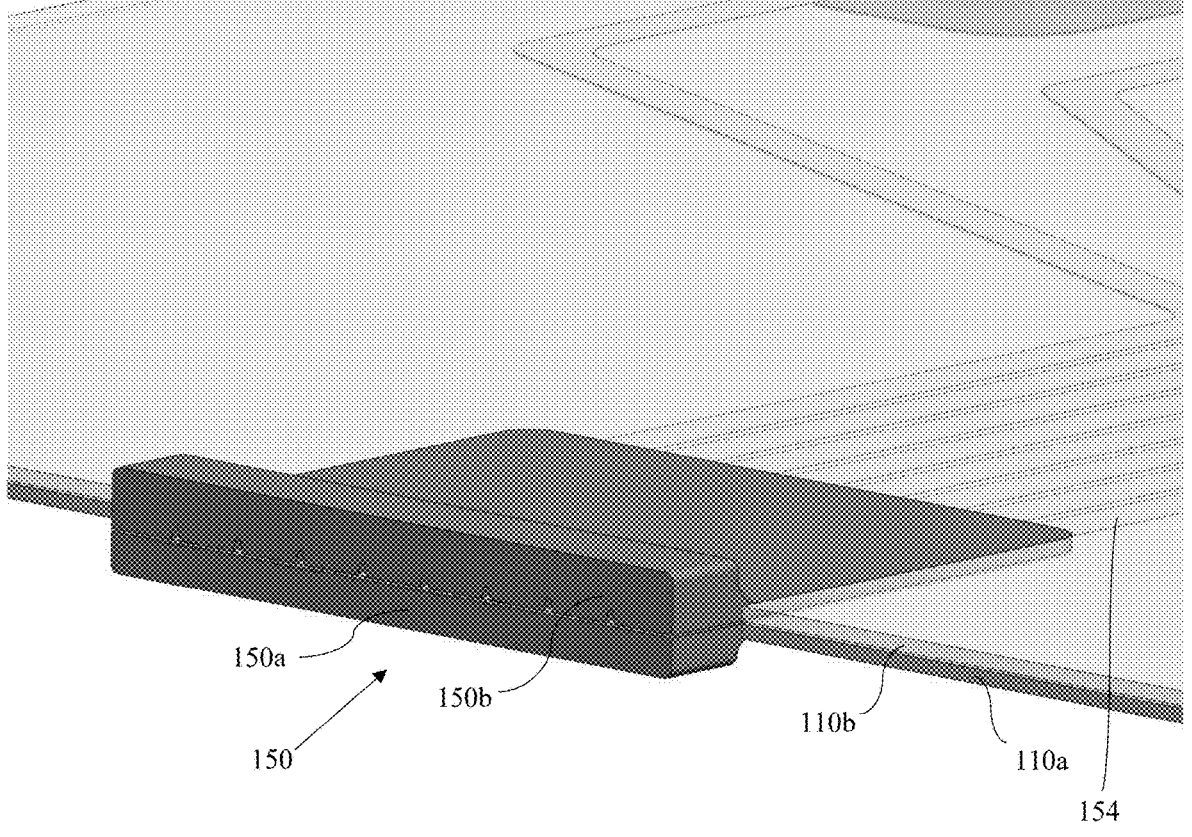
FIG. 8 depicts an interconnect coupled with a substrate that supports nerve modulation as described herein.
Figure 8:

FIG. 8 depicts a system 800 where the interconnect 150 is coupled with the first layer 110a and the second layer 110b. In some embodiments, the interconnect 150 may include one or more pin connections. A pin connection may receive one or more pins (not shown) from an external source and may facilitate the communication of signaling (e.g., via the pins) to a device connected to the pins.

As described with reference to FIGS. 4 and 6, the interconnect 150 may include a top half 150a and a bottom half 150b. The top half 150b may be at least partially in contact with the second layer 110b and the bottom half 150a may be at least partially in contact with the first layer 110a. In other examples (not shown), the interconnect 150 may be a single piece that is connected to the substrate 110 after the substrate 110 is formed. For example, the interconnect 150 may include one or more crimps (not shown) and may couple to the conductive ink 154 by crimping (e.g., crimping down) to a region where the conductive ink 154 terminates, thus forming an electrical connection between the conductive ink 154 and the interconnect 150.

Figure 9:
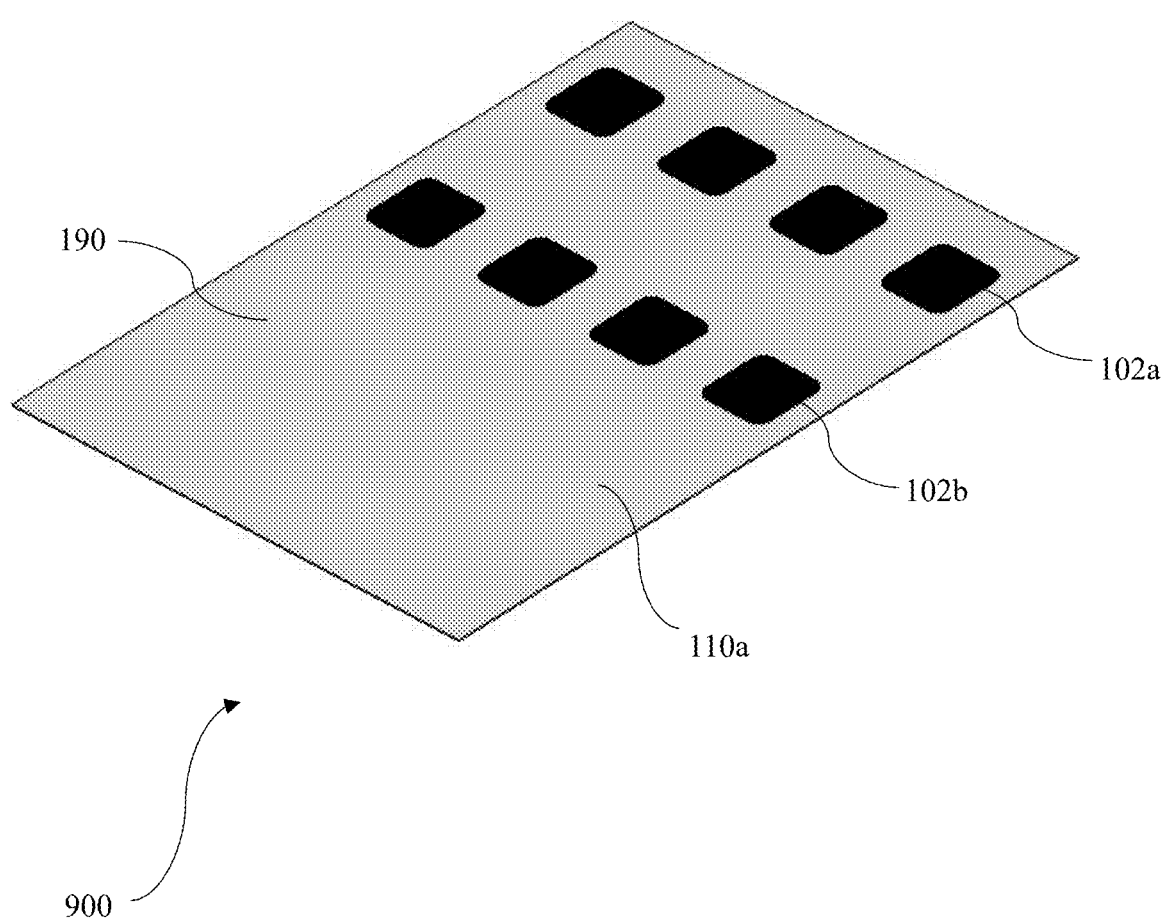
FIGS. 9 through 12 depict methods of manufacturing a substrate that supports nerve modulation as described herein.

FIG. 9 depicts a portion of a method 900 for manufacturing a substrate 110. In some embodiments, the substrate 110 may be formed from a silicone material, thus may be referred as a silicone substrate 110. The substrate 110 may be formed of any suitable materials or polymer for biocompatibility and comfortability for a user, and compatibility between any other materials (e.g., polymers) used in the method of manufacturing 900 of a substrate 110. FIG. 9 depicts a first manufacturing step, where electrodes 102 are embedded within a first layer 110*a*. The substrate 110, when formed, may be bonded with a liner or may exist independent of a liner. If bonded with a liner 101, the substrate 110 may collectively receive a residual limb (not shown) such that the substrate 110 fits underneath a region of a prosthesis 103 that also receives the residual limb. If not bonded with a liner 101, the substrate 110 may be in direct contact with a user's skin.

A base layer (e.g., a first layer 110*a*) can be formed with an array of electrodes 102. The array may consist of any number of electrodes 102, e.g., two, four, six, eight, ten, etc. The electrodes 102 can be made of a conductive silicone material, or any other suitable electrode material. In some embodiments, the electrodes can be die cut from a sheet of a suitable conductive material, such as a sheet of conductive silicone, or injection molded onto (into) the first layer 110*a*. The electrodes 102 in the first layer 110*a* may be strategically recessed to accommodate for conductive gel pads to be inserted, may be non-protruding (or essentially "level" with, coplanar with an upper surface of the first layer 110*a*), or may be protruding to promote contact.

Further, within the first layer 110*a*, non-conductive silicone, or any other suitable base layer material 190, can be injected and molded around the array of electrodes 102 to bond the materials without the use of an adhesive. In some embodiments, the base layer material 190 may be a polymeric material. In some embodiments, the base layer material 190 may be a soft silicone of 5 mm or less. The base layer material 190 can be of a softness graded anywhere on the durometer shore hardness scale (e.g., Shore 5A or less) that promotes an embodiment's desired characteristics (e.g., comfortability).

In some embodiments, the forming of the first layer 110*a* will involve a vulcanization process. The vulcanization process can improve elasticity, tear strength, resistance to organic solvents, and abrasion, among other potential benefits. In some embodiments of this method, the base layer material 190 and the array of electrodes 102 are biocompatible to improve a substrate's 110 ability to perform an intended function, without eliciting any undesirable local or systemic effects in the user of the substrate 110.

In some embodiments, sensors (not shown) may be formed in the first layer 110*a*. Depending on the type of sensor, apertures (not shown) may be formed to allow for the sensor to interact with the signal the sensor is meant to transduce. For example, a diaphragm-based pressure sensor may be placed in an aperture of the first layer 110*a* to allow acoustic pressure signals to reach the diaphragm and be converted into sensor data. The sensors may be placed at the same time as the array of electrodes.

If sensors are included in an embodiment of a substrate 110, a feedback path (not shown) for the sensor signals may be incorporated. The feedback path may be made of a conductor capable of transmitting sensor data, such as a wire or a conductive path as described in the present disclosure. In some embodiments, the sensor may communicate wirelessly with other electronics, such as via Bluetooth, if the sensor includes the required circuitry (e.g., a communication module).

In some embodiments, the substrate 110 (e.g., the first layer 110*a*) may include one or more sensors in communication with the residual limb and configured to receive one or more parameters associated with silicone substrate, the residual limb, or a combination thereof. For example, the sensors may include a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof. Additionally or alternatively, the stretch sensor may include a piezo resistive sensor, the movement sensor may include an accelerometer, a gyroscope, an optical sensor, a hall effect sensor, or a resistive flexion sensor, the oxygen sensor may include an optical oximeter, the pressure sensor may include a capacitive sensor, a force sensing resistor, an optical sensor, a pneumatic sensor, a strain-gauge sensor, a piezoelectric sensor, or a piezo chromic sensor, and the vibrational sensor may include an accelerometer or a gyroscope.

Figure 10:
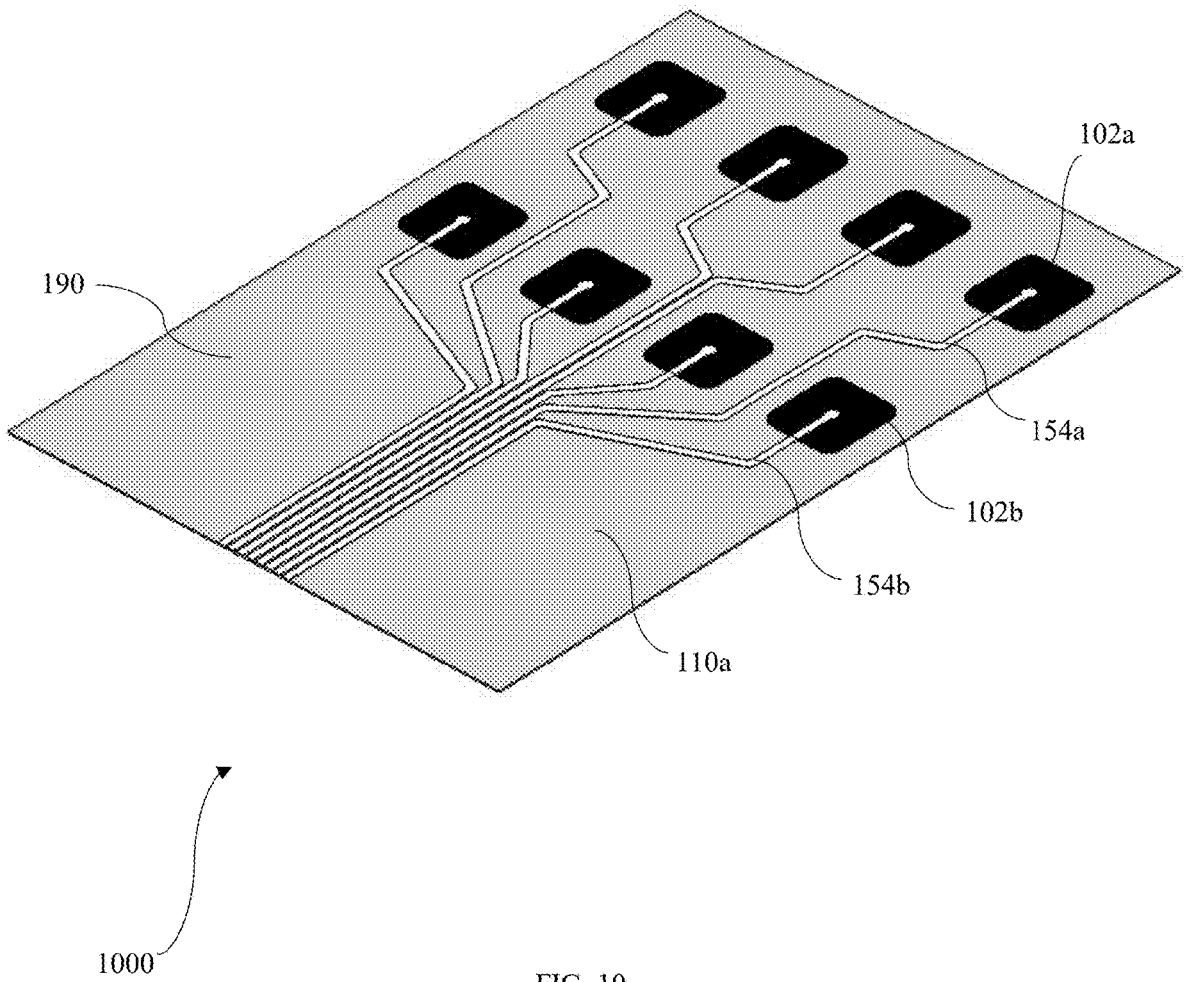

FIG. 10 depicts a portion of a method 1000 for manufacturing a substrate 110. In some embodiments, the substrate 110 may be formed from a silicone material, thus may be referred as a silicone substrate 110. FIG. 10 depicts a second manufacturing step, where conductive ink 154 is formed at the first layer 110*a*.

A screen-printed layer may be formed on the first layer 110*a*. In the screen-printed layer, a conductive path may be formed between the array of electrodes 102 in the first layer 110*a* and an edge (e.g., a side) of the first layer 110*a*. The conductive path may touch directly to the electrodes 102, without requiring a connector. In some embodiments, the conductive path may be formed with flexible conductive silicone ink 154 via screen printing. In some embodiments, the screen-printed layer will be heat cured for approximately one hour at approximately 300 degrees Fahrenheit.

The conductive ink 154 may be applied in the screen-printed layer by other methods than screen printing, such as syringe dispensing, dipping, spraying, etc. In some embodiments, the conductive path will be formed with conductive wire, paint, or any other suitable method to form a conductive path between the electrodes 102 and the interconnect 150.

Figure 11:
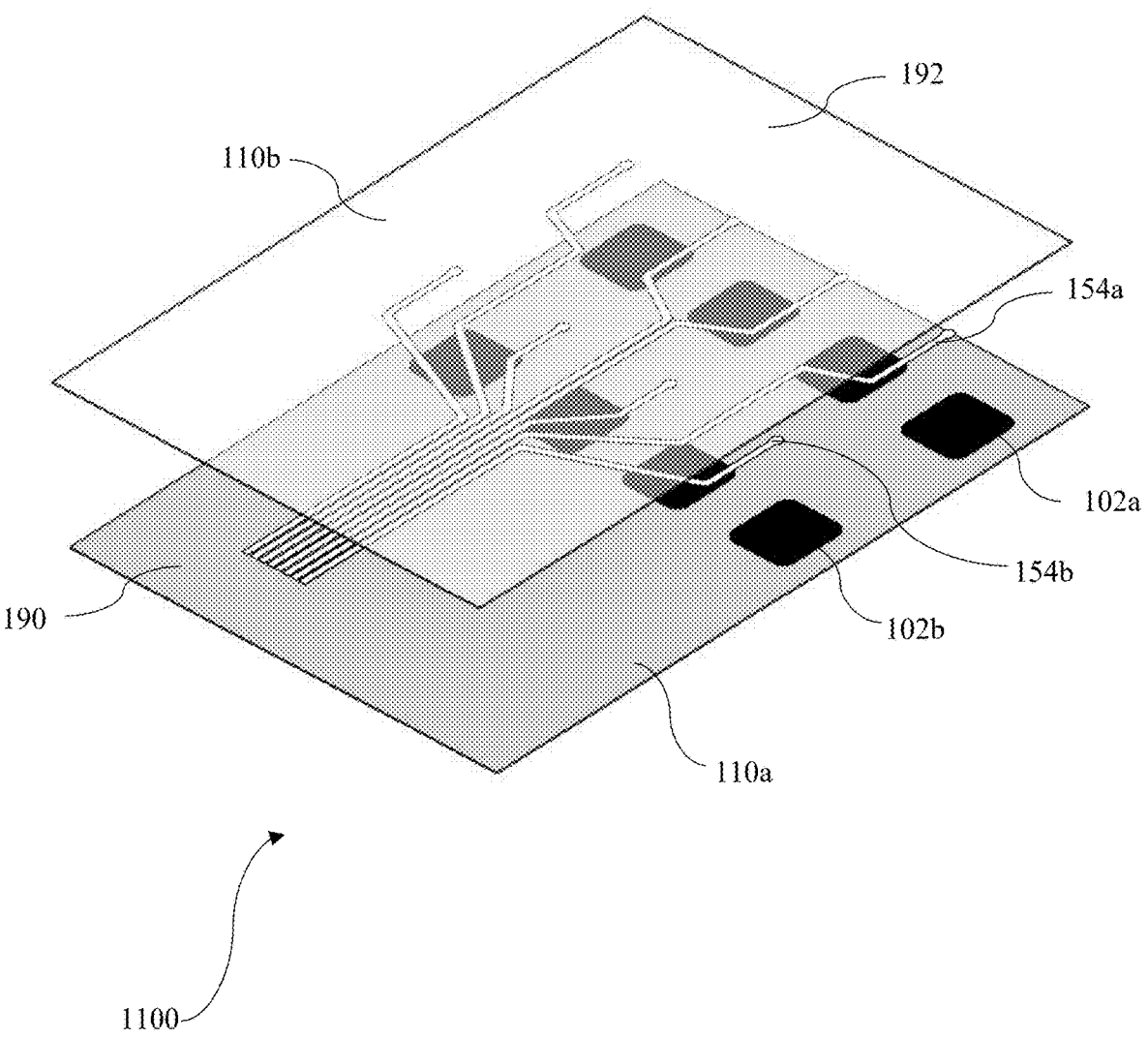

FIG. 11 depicts a portion of a method 1100 for manufacturing a substrate 110. In some embodiments, the substrate 110 may be formed from a silicone material, thus may be referred as a silicone substrate 110, although it should be appreciated that the substrate may be formed of any suitable material (e.g., polymeric material). FIG. 11 depicts a third manufacturing step, where a second layer 110*b* is formed over the conductive ink 154 and the first layer 110*a*. A second layer 110*b* may include a top layer material 192 of the same or different material as the base layer material 190 of the first layer 110*a*, and can be formed over the screen-printed layer. A second layer 110*b* may serve as a protective barrier for the electrodes and the conductive ink. In some embodiments with a liner, the second layer 110*b* may serve as a protective barrier between the liner, and the electrodes and the conductive ink.

Figure 12:
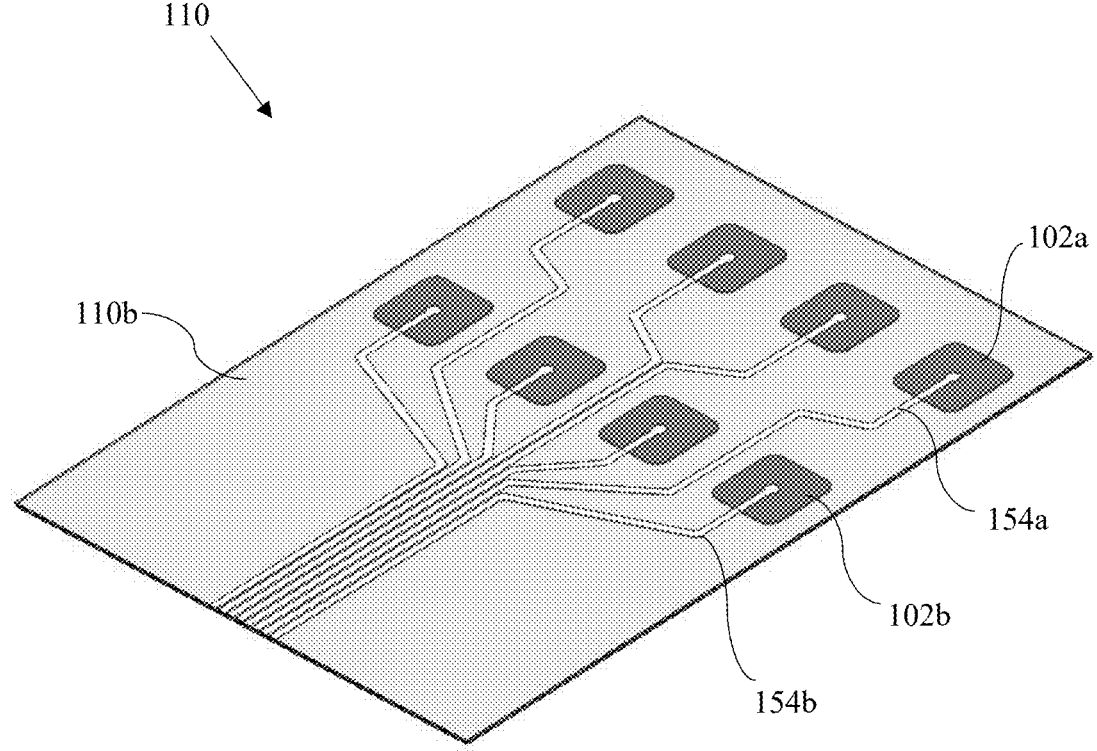
Figure 12:
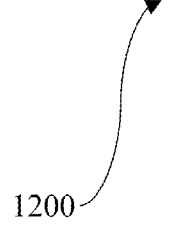

FIG. 12 depicts a completed embodiment of a method 1200 for manufacturing a substrate 110 after the second layer 110*b* is formed over the conductive ink 154 and the first layer 110*a*. In other embodiments (not shown), the substrate 110 may be formed into a tubular shape by connecting two or more edges together via a seam. Additionally or alternatively, the substrate 110 may be bonded with a liner 101.

Figure 13:
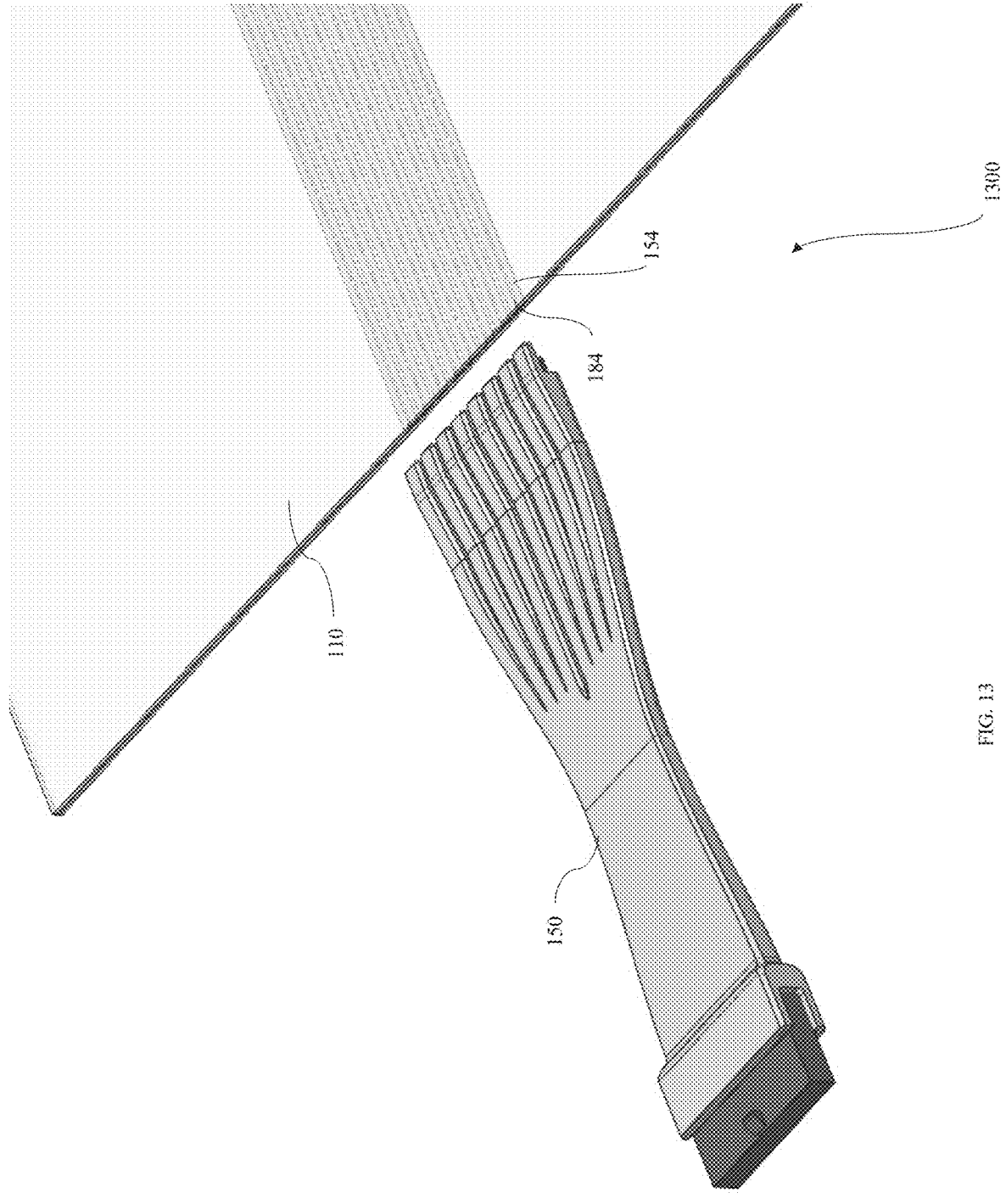

FIG. 13 depicts a system 1300 having an external interconnect 150 configured to connect (e.g., couple) with the substrate 110. In some examples, the external interconnect 150 may couple with an external controller configured to activate the electrodes of the substrate 110. The external interconnect may include one or more pins (not shown) that engage with the substrate 110 such that each pin is associated with (e.g., in contact with, electronically connected to) a respective portion of the conductive ink 154. In some embodiments, each trace of the conductive ink may be associated with a portion of a channel 184 configured to receive the pins. That is, each trace may be associated with a respective portion of the channel 184 such that an opening of each portion of the channel 184 receives a respective pin.

In some examples, the external interconnect 150 may be generally flexible. For example, each pin may be associated with a respective flexible portion (e.g., a finger) that is configured to move and flex in different directions. The flexibility of the pins may allow for each pin to more easily align with and be inserted into a respective channel.

In some embodiments, the channels 184 may be made of a polymer material, or may otherwise be relatively rigid in order to receive the pin(s). Additionally or alternatively, the channels 184 may allow for the substrate 110 to be cut (e.g., trimmed) to a desired length. For example, a user may trim the substrate 110 to a desired length. In some embodiments with channels 184, when trimmed, the channels 184 may still provide an opening to receive the pin(s) and couple (e.g., connect) the pin(s) with respective traces of the conductive ink 154.

In some embodiments, the external interconnect 150 may couple with or otherwise connect to a circuit board assembly 130, which may be associated with or otherwise be referred to as an electrode controller 104. The circuit board assembly 130 may include a battery 131 in electrical communication with the printed circuit board assembly 130. When the electrode controller 104 is in electrical communication with the embedded wires or the conductive ink 154, then a microprocessor (not shown) of the printed circuit board assembly 130 of the electrode controller 104 controls the transmission of electrical current between the battery 131 and the embedded wires or conductive ink 154 to control whether an electrode of the array of electrodes will transmit electrical current, which the electrode receives from the battery 131, and whether an electrode of the array of electrodes will receive electrical current, which the electrode transmits to the battery 131.

Figure 14A:
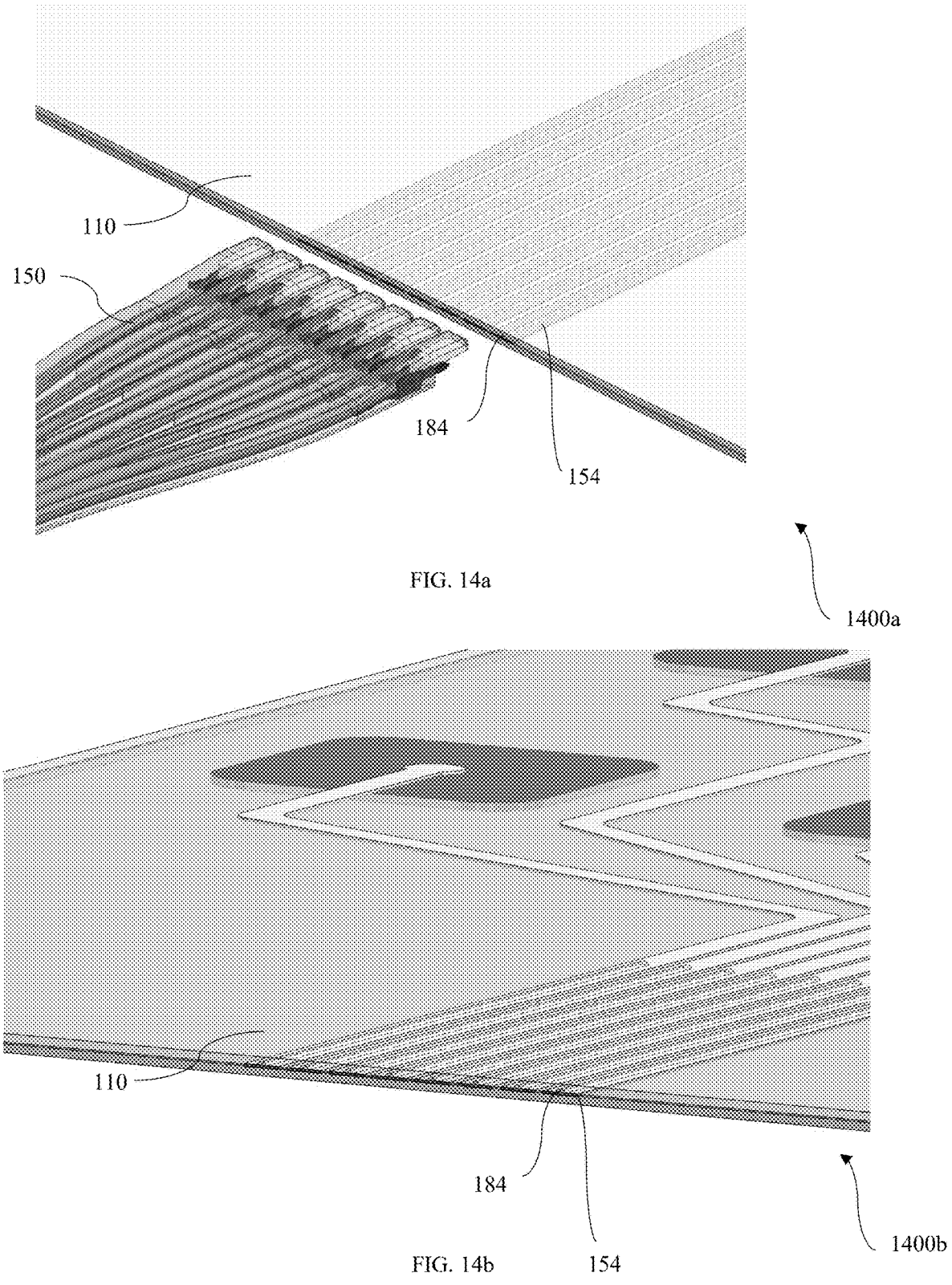

FIG. 14*a* depicts a system 1400*a* having an external interconnect 150 configured to connect (e.g., couple) with the substrate 110. In some examples, the external interconnect 150 may be generally flexible. For example, each pin may be associated with a respective flexible portion (e.g., a finger) that is configured to move and flex in different directions. The flexibility of the pins may allow for each pin to more easily align with and be inserted into a respective channel. FIG. 14*b* depicts a system 1400*b* having respective channels 184 configured to receive an external interconnect 150. As described herein, each conductive trace (e.g., each trace of conductive ink 154) may be coupled with a respective electrode 102, and each conductive trace may be associated with a respective channel 184. When a channel 184 receives a pin of the external interconnect 150, the external interconnect 150 may be in electrical communication with the associated electrode 102.

In some embodiments, the channels 184 may be incorporated into the substrate 110 during one or more manufacturing steps as described with reference to FIGS. 9 through 11. For example, the channels 184 may be adapted to the base layer 110*a* or the top layer 110*b*. That is, when manufacturing the base layer 110*a* or the top layer 110*b*, the channels 184 may be integrated into the respective layer. In other examples, the channels 184 may be placed above the base layer 110*a* after it is manufactured, and the top layer 110*b* may later be placed over the base layer 110*a* such that the channels are located between the respective layers. In some embodiments, the channel 184 may be formed by placing an object on top of a conductive trace 154 before the top layer material 192 is deposited, then depositing the top layer material 192, then removing the object once the top layer 110*b* is formed-leaving a channel 184 in the empty space.

Figure 15:
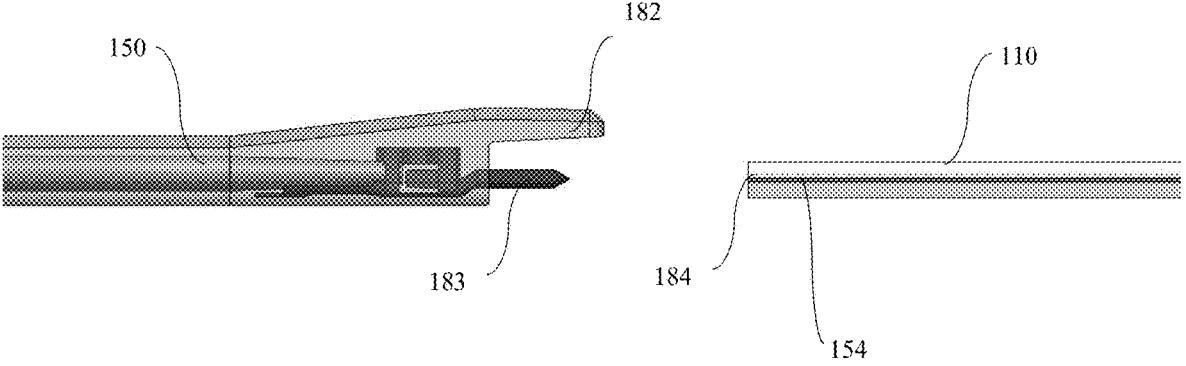
Figure 15:
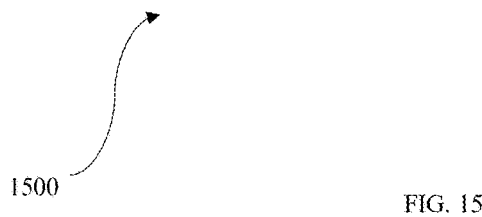

FIG. 15 depicts a system 1500 having an external interconnect 150 configured to connect (e.g., couple) with the substrate 110. In some examples, the external interconnect 150 may couple with an external controller configured to activate the electrodes of the substrate 110. The external interconnect may include one or more pins 183 that engage with respective channels 184 of the substrate 110 such that each pin is associated with (e.g., in contact with, electronically connected to) a respective portion of the conductive ink 154. In some embodiments, the external interconnect 150 may include a lip 182 (e.g., a cover) that comes in contact with a surface of the substrate 110 when the pins 183 are engaged with the channels 184. In some embodiments, the lip 182 may include or otherwise receive an adhesive such that the external interconnect 150 is connected (e.g., temporarily connected to, adhered to) the substrate 110. In some embodiments, the adhesive may be broken, the external interconnect 150 removed, and later reengaged and adhered to the substrate 110.

Figure 16A:
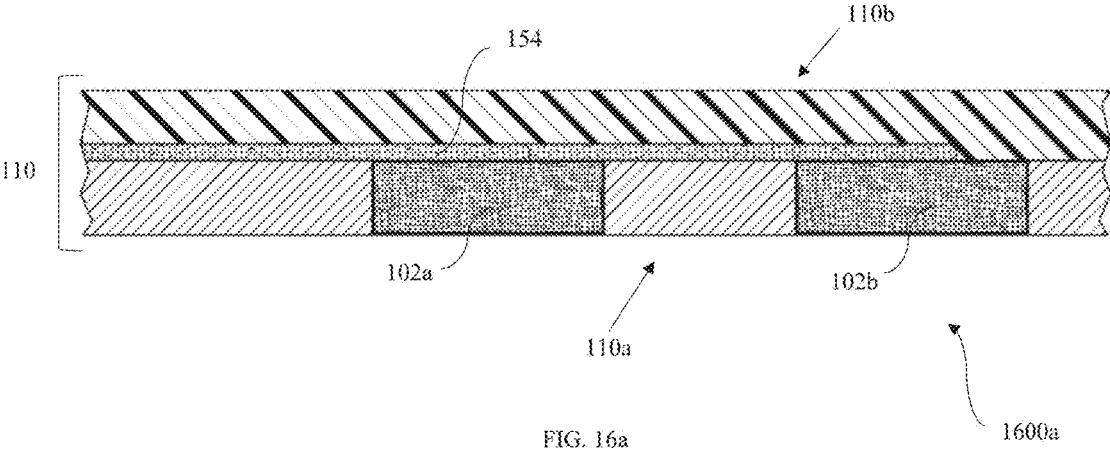
FIGS. 16A and 16B depict partial cross-sectional views of a substrate that supports nerve modulation as described herein.
Figure 16B:
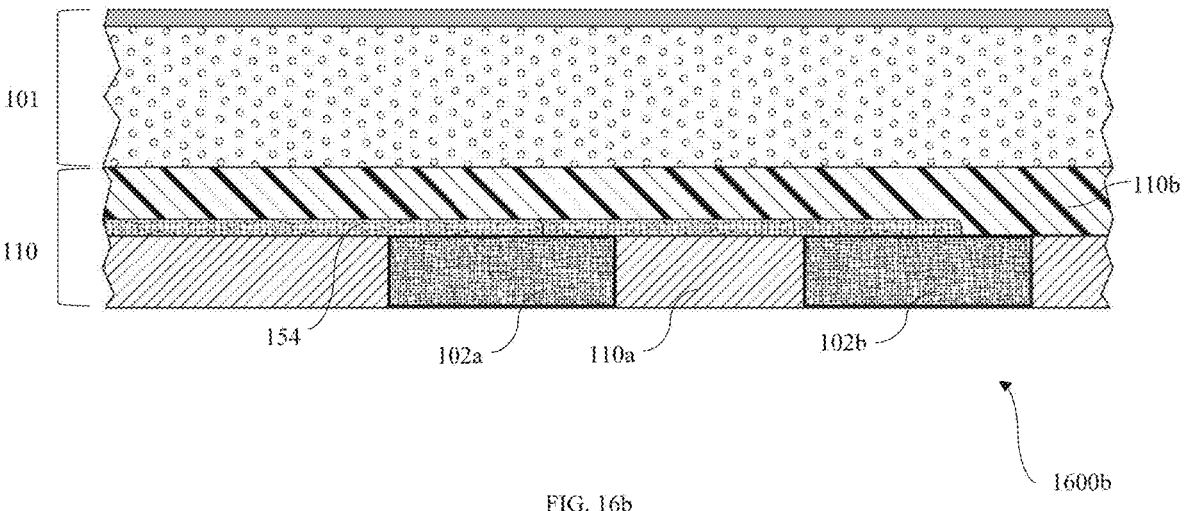

FIG. 16*a* depicts a partial cross-sectional view of a substrate 110 of a system 1600*a*. FIG. 16*b* depicts a partial cross-sectional view of a substrate 110 with a liner 101 bonded to the substrate 110 of a system 1600*b*. For example, FIGS. 16*a* and 16*b* depict a location of the electrodes 102 relative to the conductive ink 154 and the second layer 110*b*. In some embodiments, the electrodes 102 may be in direct contact with the conductive ink 154 such that the electrodes 102 are adapted directly to the conductive ink 154. Thus, the electrodes 102 may stimulate a user's skin or residual limb based on signaling received from the electrode controller 104 via the conductive ink 154.

The electrodes 102 may be recessed relative to the base layer 110*a*. That is, an upper surface of each electrode 102 may be below a bottom surface of the base layer 110*a* (shown in FIG. 17). Moreover, the electrodes 102 may be generally aligned with a bottom surface of the base layer 110*a*. That is, an upper surface of each electrode 102 may be generally aligned with (e.g., even with, coplanar with, aligned with) an upper surface of the base layer 110*a*. Moreover, the electrodes 102 may protrude relative to a bottom surface of the base layer 110*a*. The base layer 110*a* may contact a user's skin or a user's residual limb.

Figure 17:
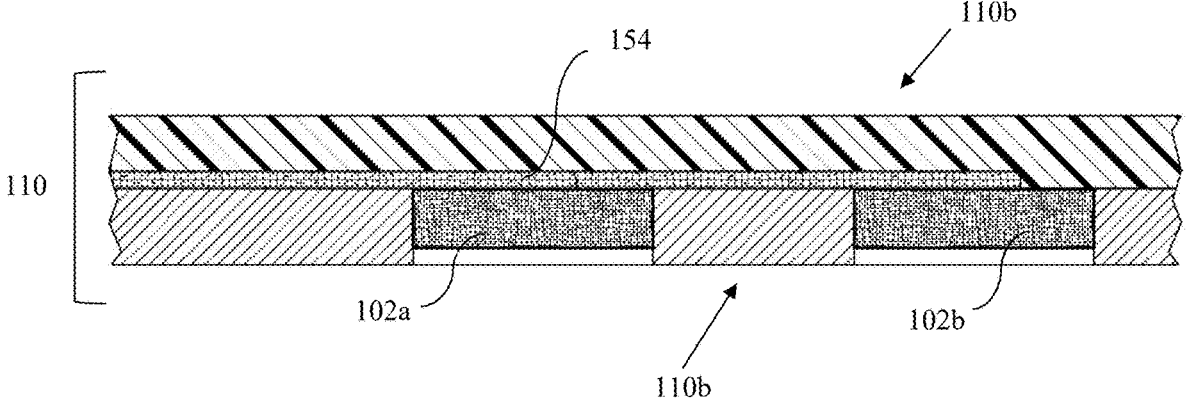
FIG. 17 depicts a partial cross-sectional view of an electrode of a substrate that supports nerve modulation as described herein.
Figure 17:

FIG. 17 depicts a partial cross-sectional view of a substrate 110. For example, FIG. 17 depicts a location of the electrodes 102 relative to the conductive ink 154 and the second layer 110b. In some embodiments, the electrodes 102 may be in direct contact with the conductive ink 154 such that the electrodes 102 are adapted directly to the conductive ink 154. Thus, the electrodes 102 may stimulate a user's skin or residual limb based on signaling received from the electrode controller 104 via the conductive ink 154.

The electrodes 102 may be recessed relative to the base layer 110a as is shown in the embodiment of FIG. 17. That is, an upper surface of each electrode 102 may be below a bottom surface of the base layer 110a. Moreover, the electrodes 102 may be generally aligned with a bottom surface of the base layer 110a. That is, an upper surface of each electrode 102 may be generally aligned with (e.g., even with, coplanar with, aligned with) a bottom surface of the base layer 110a. Moreover, the electrodes 102 may protrude relative to a bottom surface of the base layer 110a. The base layer 110a may contact a user's skin or a user's residual limb.

In some embodiments, each electrode 102 may be adjacent to a recess. That is, a portion of the recesses may be generally aligned with a bottom surface of the base layer 110a. The recesses may house an insert, such as a hydrogel insert or work to retain a conductive topical, for example.

Figure 18:
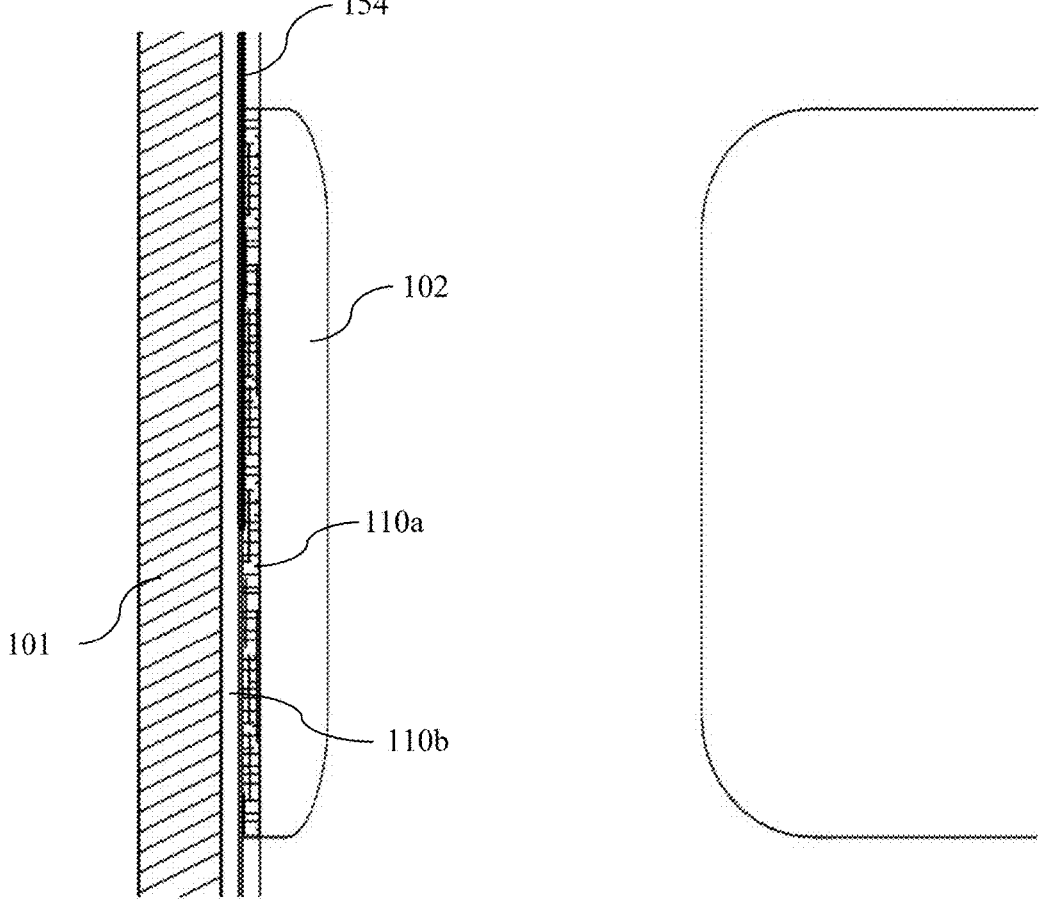
FIG. 18 depicts a cross-sectional view of an electrode of a substrate that supports nerve modulation as described herein.
Figure 18:
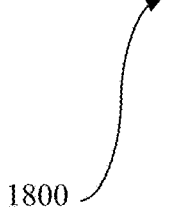

FIG. 18 depicts a partial cross-sectional view of an electrode 102 of a substrate 110. For example, FIG. 18 depicts a location of an electrode 102 relative to the conductive ink 154, the first layer 110a, the second layer 110b, and a liner 101. In some embodiments, the electrodes 102 may be in direct contact with the conductive ink 154 such that the electrode 102 is adapted directly to the conductive ink 154. The electrode 102 may extend below a bottom surface of the first electrode material 110a such that it makes contact (e.g., direct contact) with a user's skin or a user's residual limb.

Figure 19:
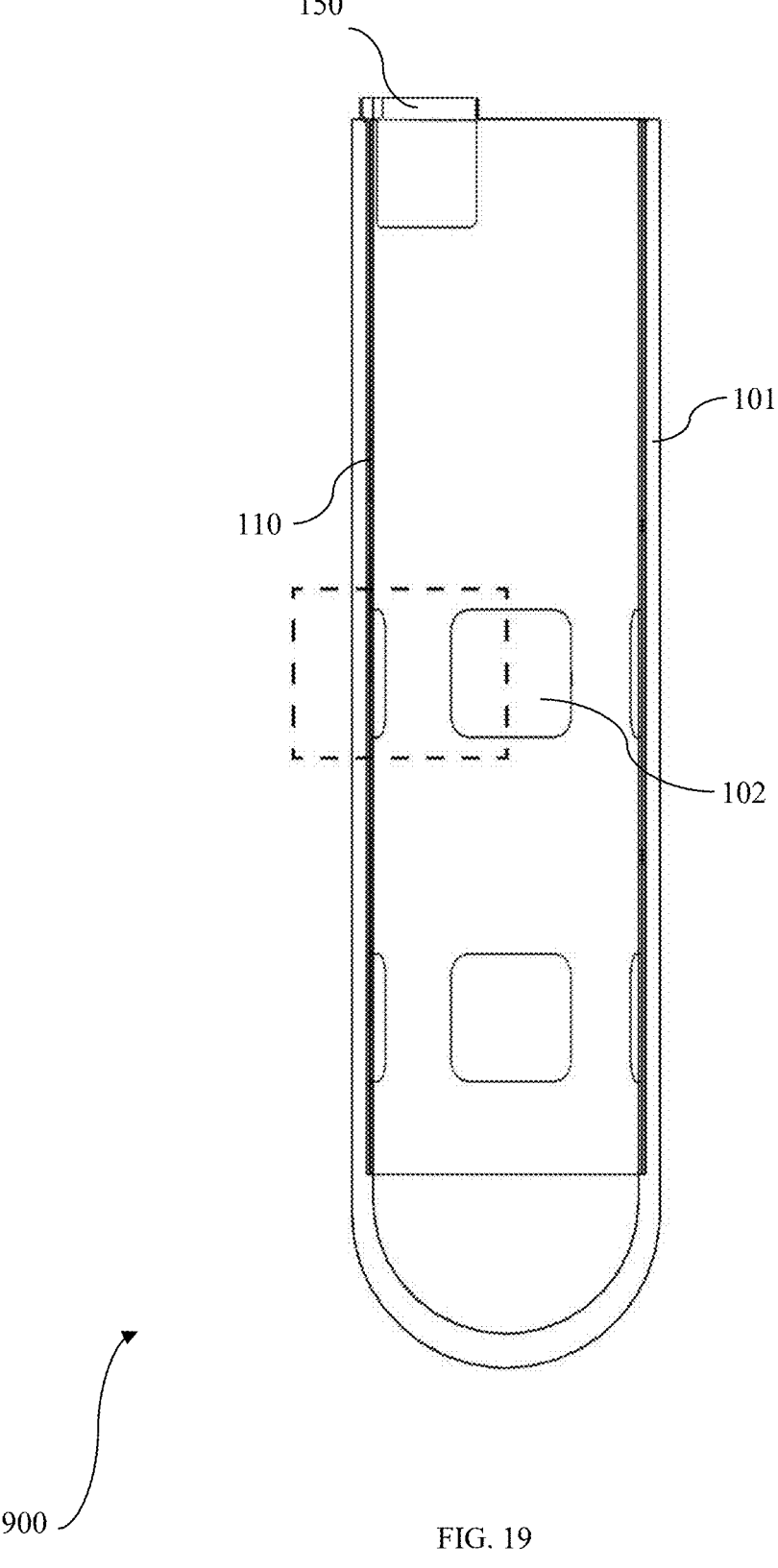
FIG. 19 depicts a cross-sectional view of an electrode of a substrate that supports nerve modulation as described herein.

FIG. 19 depicts a partial cross-sectional view of an electrode 102 of a substrate 110 that includes an interconnect 150. For example, FIG. 19 depicts a location of an electrode 102 relative to the liner 101 when formed in a tubular shape. In some embodiments, a user's residual limb may be inserted into the liner 101 and substrate 110 such that the electrode 102 may stimulate nerve fibers within the user's residual limb. In the embodiment of FIG. 19, a partially integrated interconnect 150 is shown.

Figure 20:
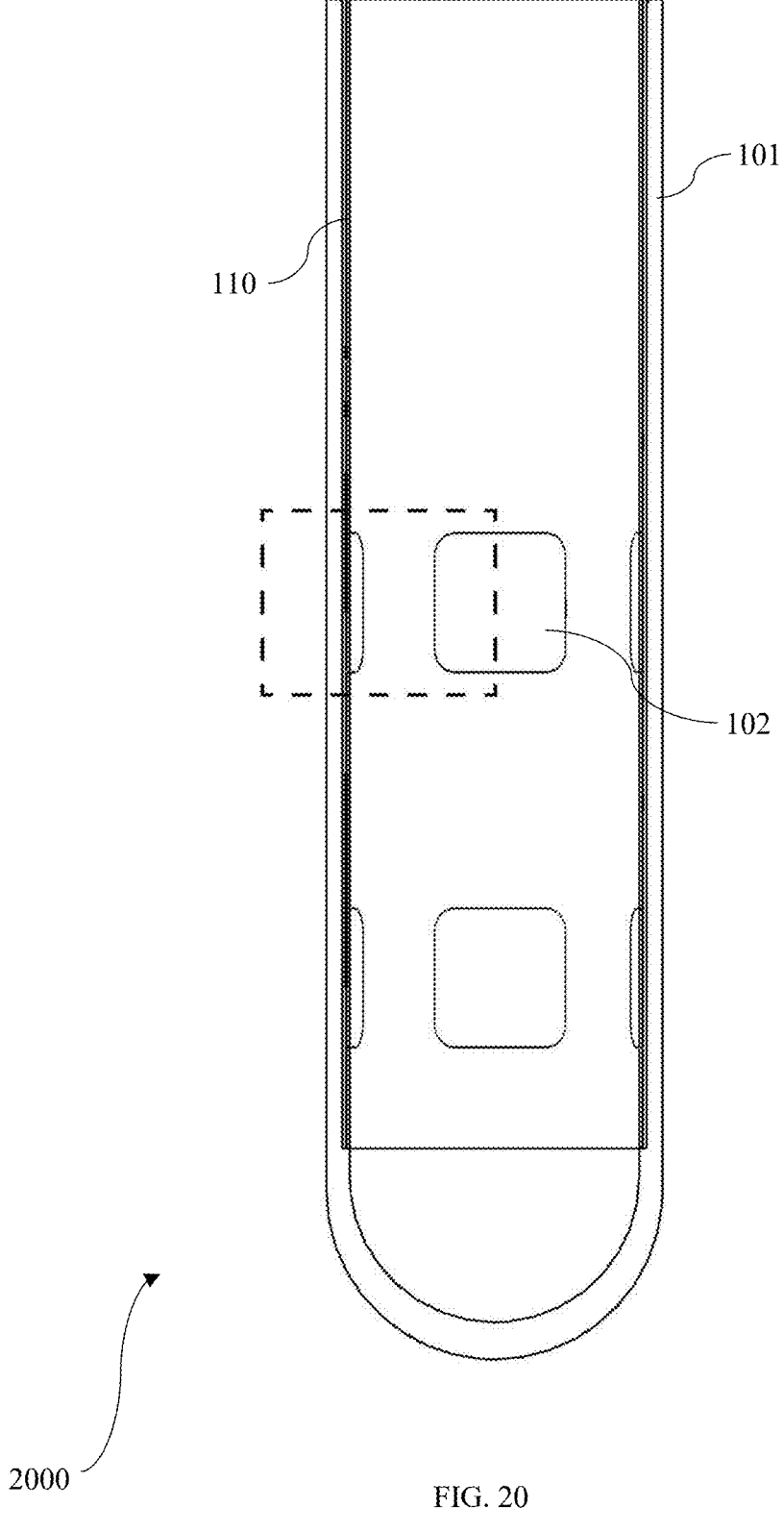
FIG. 20 depicts a cross-sectional view of an electrode of a substrate that supports nerve modulation as described herein.

FIG. 20 depicts a partial cross-sectional view of an electrode 102 of a substrate 110. For example, FIG. 19 depicts a location of an electrode 102 relative to the liner 101 when formed in a tubular shape. In some embodiments, a user's residual limb may be inserted into the liner 101 and substrate 110 such that the electrode 102 may stimulate nerve fibers within the user's residual limb. In the embodiment of FIG. 20, channels 184 (not shown) may be implemented to connect the electrodes 102 with an electrode controller 104.

Figure 21:
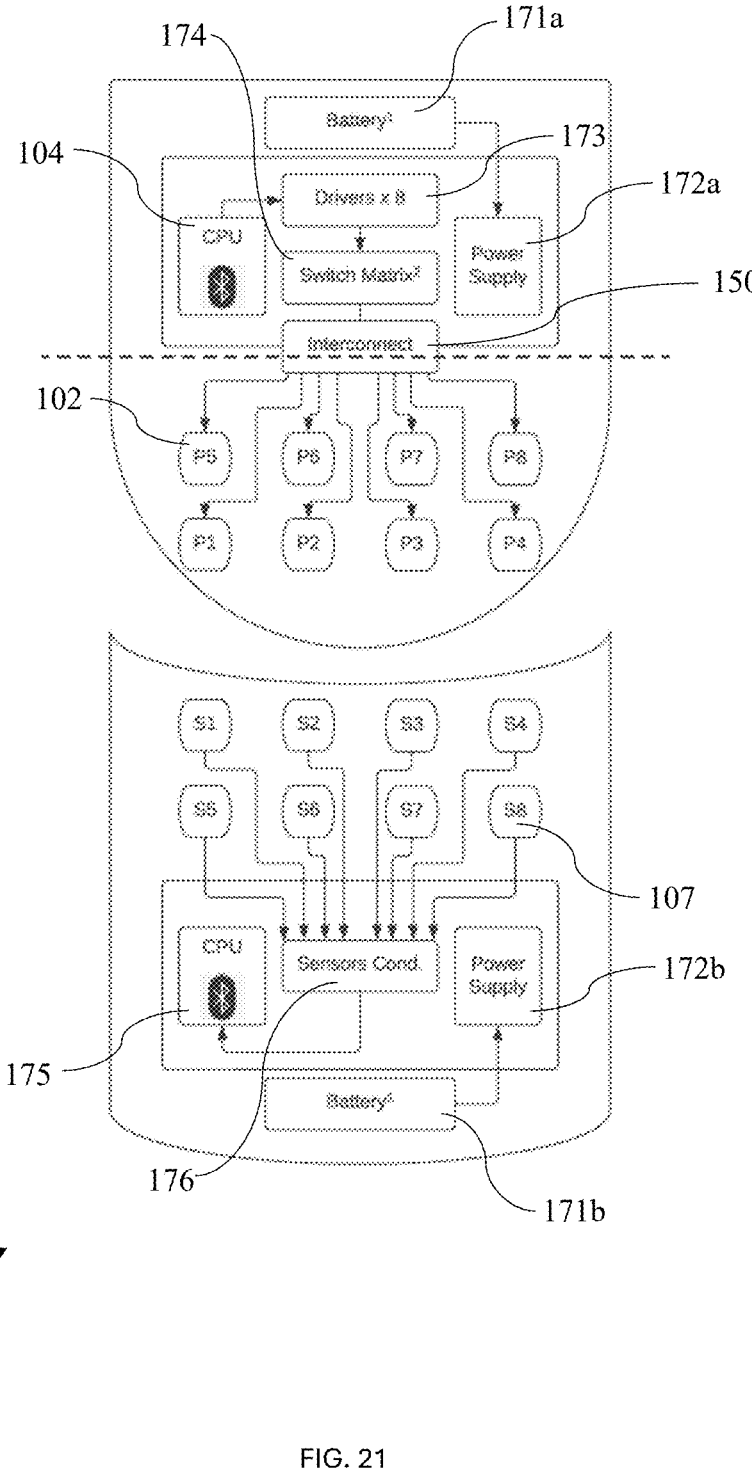
FIG. 21 depicts a system that supports nerve modulation as described herein.

FIG. 21 depicts a system 2100, which illustrates aspects of a substrate 110 as described herein. In some examples, the system 2100 may illustrate one or more electrodes 102 that are coupled with an interconnect 150. The electrodes 102 may be coupled with a switching matrix 174 that is in communication (e.g., electrical communication) with one or more drivers 173. The drivers 173 may be coupled with an electrode controller 104 and a power supply 172. In some instances, the power supply 172a may be a battery or may be coupled with a battery 171a.

The switching matrix 174 may be configured to activate any of the electrodes 102 (or any combination of the electrodes 102). For example, the switching matrix 174 may include a plurality of switches (e.g., H-Bridge circuits), and each switch may correspond to one of the electrodes 102. Each switch may be coupled with a respective driver 173 via a wire, a conductive trace, or another type of electrical connection. In some embodiments, a driver 173 (or a combination of drivers 173) may be activated to provide an electrical current (e.g., a signal) to a respective switch of the switching matrix 174. The signal may activate the switch, which may open (or close) the switch, resulting in a particular pin of the interconnect 150 being driven (e.g., driven to a relatively high or low value). The pin may correspond to a respective trace (e.g., of the conductive ink 154), and an electrode 102 coupled with (e.g., adapted to) the trace may be activated. When a driver 173 is not activated, the corresponding switch of the switching matrix 174 may be closed (or open) and the corresponding electrode 102 may not be activated. It should be appreciated that the switching matrix 174 may be connected to and incorporated with the sensors 107 in order to direct data signaling as desired.

In some embodiments, any combination of electrodes 102 may be activated. For example, the electrode controller 104 may receive signaling (e.g., from a GUI of a user device, from an artificial intelligence algorithm), indicating which electrodes 102 to activate. In such examples, one or more of the drivers 173 may be activated, which may result in a switch or a combination of switches of the switching matrix 174 being activated. In some embodiments, the electrode controller 104 may be configured to directly signal to the switching matrix 174. Based on the switch or combination of switches being activated, one or more electrodes 102 may be activated to stimulate the nerve fibers in a residual limb of an amputee or of a user's skin.

In some embodiments, the system 2100 may include a power supply 172a. For example, the power supply 172a may be used to power the electrode controller 104, the drivers 173, and the switching matrix 174. In some examples, the power supply 172a may be coupled to an external power source, such as an outlet or power source worn or carried by a user. In other embodiments, the power supply 172a may be coupled with a battery 171a. The battery 171a may be located in or otherwise attached to the substrate 110 such that the substrate 110 is not connected to any external power sources (e.g., via a wire or cord). In some embodiments, the battery 171a may be rechargeable, replaceable, or both.

The electrode controller 104 may include circuitry to communicate with a user device wirelessly. For example, the electrode controller 104 may support a Bluetooth or Wi-Fi connection with a user device, such as a mobile phone or a wearable device. In some embodiments, the electrode controller 104 may communicate with a user device via a wired connection. In either case, the electrode controller 104 may receive signaling (e.g., from the user device) to activate one or more electrodes 102 for stimulating the nerve fibers of a residual limb of an amputee or of the user's skin.

FIG. 21 also illustrates a cover with one or more sensors 107 that are coupled with a controller 175 (e.g., a sensor controller). The sensors 107 may be coupled with a switching matrix (not shown) or other component that is in communication with the controller. The controller 175 may be coupled with a power supply 172b. In some instances, the power supply 172b may be a battery or may be coupled with a battery 171b.

The switching matrix may be configured to route signaling from any of the sensors 107 (or any combination of the sensors 107) to the controller 175. For example, the switching matrix may include a plurality of switches, and each switch may correspond to one of the sensors 107. Each switch may be coupled with a respective sensor 107 via a wire, a conductive trace, or another type of electrical connection.

In some embodiments, any combination of sensors 107 may be activated. For example, the controller 175 may receive signaling (e.g., from a GUI of a user device), indicating which sensors 107 are active. In such examples, a switch or a combination of switches of the switching matrix may be activated. Based on the switch or combination of switches being activated, one or more feedback from one or more sensors 107 may be provided to the controller 175.

In some embodiments, the system 2100 may include a power supply 172b. For example, the power supply 172b may be used to power the controller 175 and the switching matrix. In some examples, the power supply 172b may be coupled to an external power source, such as an outlet or power source worn or carried by a user. In other embodiments, the power supply 172b may be coupled with a battery 171b. The battery 171b may be located in or otherwise attached to the substrate 101 such that the substrate 101 is not connected to any external power sources (e.g., via a wire or cord). In some embodiments, the battery 171b may be rechargeable, replaceable, or both.

The controller 175 may include circuitry to communicate with a user device, with the electrode controller 104, or both. For example, the controller 175 may support a Bluetooth or Wi-Fi connection with a user device and the electrode controller 104, such as a mobile phone or a wearable device. In some embodiments, the controller 175 may communicate with a user device and/or the electrode controller 104 via a wired connection. In either case, the controller 175 may receive signaling (e.g., from the user device, from the electrode controller 104, or both) to activate one or more sensors 107. In other embodiments, the controller 175 may communicate data collected from the sensors 107 to a user device for display. The controller 175 may communicate the data directly to the user device, or may communicate the data to the user device via the electrode controller 104.

Figure 22:
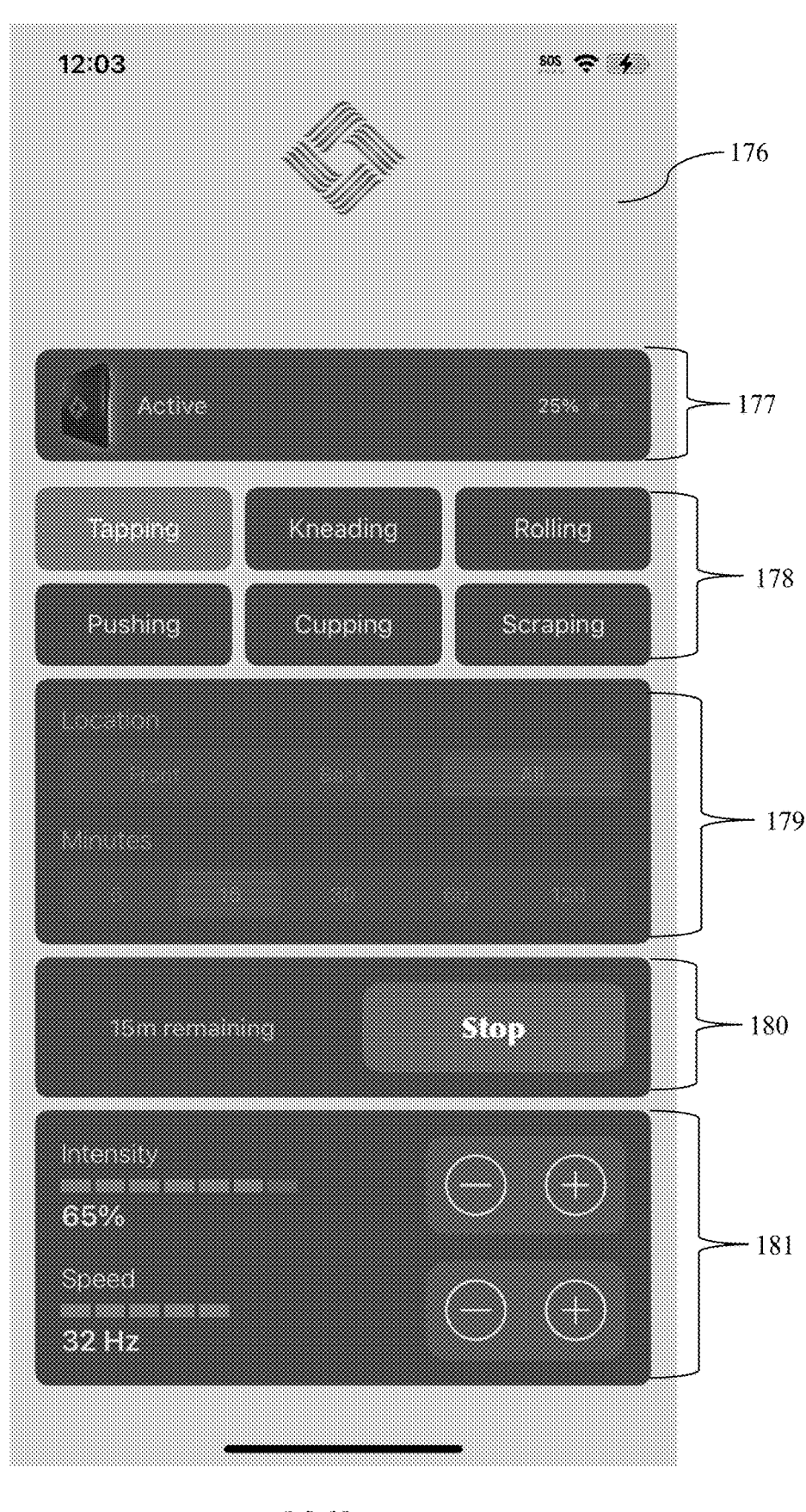
FIG. 22 depicts a graphical user interface that supports nerve modulation as described herein.

FIG. 22 depicts a graphical user interface 176, which may be in communication (e.g., electrical communication) with aspects of a substrate 110 as described herein. In some examples, the user interface 176 may be associated with a user device, such as a mobile device (e.g., a cell phone), a computer, or a wearable device. The user interface 176 may include one or more fields, and may be configured to receive one or more inputs by a user and display one or more settings or measurements of the substrate 110. For example, the user interface 176 may receive inputs for activating or otherwise controlling aspects of the electrodes 102. The user interface 176 may also display one or more settings associated with the electrodes 102, and may display data associated with readings from one or more sensors 107.

The user interface 176 may include a first display 177 that is associated with a status of the substrate 110. For example, the first display 177 may include an indication of whether the substrate 110 is active or inactive (e.g., on or off). The first display 177 may also include an indication of a status of the battery 171. That is, the first display 177 may include an indication (e.g., a percentage indication) of a charge of the battery 171.

The user interface 176 may include a second display 178 that is associated with a type of stimulation of the electrodes 102 of the substrate 110. For example, the second display 178 may include a listing of the types of simulation the electrodes 102 are configured to perform. The electrodes 102 may perform a tapping sensation, a kneading sensation, a rolling sensation, a pushing sensation, a cupping sensation, a scraping sensation, or another type of sensation. The second display 178 may indicate which sensation is selected (e.g., by highlighting or otherwise changing the color of the associated portion of the second display 178). Additionally or alternatively, the second display 178 may receive an input from a user to select or otherwise change the type of sensation performed by the electrodes 102.

The user interface 176 may include a third display 179 that is associated with a location and a duration of active electrodes 102 of the substrate 110. For example, the third display 179 may include a listing of the location of the active electrodes 102. The active electrodes 102 may be on a front or back portion of the substrate 110. In other embodiments, all electrodes 102 may be active. The third display 179 may indicate which electrodes 102 are active (e.g., by highlighting or otherwise changing the color of the associated portion of the third display 179). Additionally or alternatively, the third display 179 may receive an input from a user to select or otherwise change which electrodes 102 are active.

In other examples, the third display 179 may include a listing of the durations for which the electrodes 102 may be activated. The electrodes 102 may be activated for 5 minutes, 15 minutes, 30 minutes, 60 minutes, or 120 minutes. In other embodiments, the electrodes 102 may be activated for any duration. The third display 179 may indicate a duration for which the electrodes 102 are to be active (e.g., by highlighting or otherwise changing the color of the associated portion of the third display 179). Additionally or alternatively, the third display 179 may receive an input from a user to select or otherwise change the duration for which electrodes 102 are active.

The user interface 176 may include a fourth display 180 that is associated with a remaining duration of active electrodes 102 of the substrate 110. For example, the fourth display 180 may include a listing of a remaining duration that the electrodes 102 will be active. The fourth display 180 may also include an input for stopping the electrodes 102 (e.g., deactivating the electrodes 102). That is, the fourth display 180 may receive an input from a user to deactivate or otherwise stop the electrode 102 stimulation.

The user interface 176 may include a fifth display 181 that is associated with an intensity and speed of active electrodes 102 of the substrate 110. For example, the fifth display 181 may include a listing of the intensity of the electrode 102 stimulation. The fifth display 181 may also include a listing of the speed of the electrode 102 stimulation. The fifth display 181 may indicate the intensity and speed that is selected (e.g., by highlighting or otherwise changing the color of the associated portion of the fifth display 181, or via a digital reading indicating a percentage of the intensity and a hertz (Hz) reading of the speed). Additionally or alternatively, the fifth display 181 may receive an input from a user to select or otherwise change the intensity and the speed of the sensation performed by the electrodes 102.

The user interface 176 may also include one or more displays associated with sensors 107 of the substrate 110. For example, the user interface 176 may include a display for indicating data (e.g., readings) from one or more sensors 107. In some embodiments, the user interface 176 may include one or more readings associated with a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, and/or a magnetic flux sensor. The user interface 176 may display a reading from a respective sensor as an absolute value (e.g., X degrees, Y pounds per square inch (PSI)) or as a percentage (e.g., Z percent).

The user device associated with the user interface 176 may include a controller (e.g., a second controller) that is configured to communicate signaling with the electrode controller 104. For example, the second controller may transmit signaling to the electrode controller 104 to activate or deactivate one or more electrodes 102, activate or deactivate one or more sensors 107, adjust or switch a type of stimulation, adjust or switch a location of active (or inactive) electrodes 102, adjust or switch a duration for which electrodes 102 are active, deactivate one or more active electrodes 102, adjust or switch an intensity at which one or more electrodes 102 are stimulating a user, and/or adjust or switch a speed at which one or more electrodes 102 are stimulating a user.

In some embodiments, the user interface 176 may include displays for eliciting user feedback (not shown), such as via a Visual Analog Scale, for example. A user feedback display may be used to improve the functionality of a machine learning/artificial intelligence algorithm and/or track progress over time (e.g., whether pain associated with Phantom Limb Syndrome is decreasing). In some embodiments, a display for eliciting user feedback may be used to track the mental health of users. In some embodiments, a display for eliciting user feedback may be used to track preferred or undesired user settings. In some embodiments, a display for eliciting user feedback may be used to compare with sensor data, and make inferences about user health. It should be appreciated that many functionalities can be implemented with user feedback, and the foregoing examples are not meant to be exhaustive.

The functions described herein may be implemented in hardware, software executed by a processing system (e.g., one or more processors, one or more controllers, control circuitry, processing circuitry, logic circuitry), firmware, or any combination thereof. If implemented in software executed by a processing system, the functions may be stored on or transmitted over as one or more instructions (e.g., code) on a computer-readable medium. Due to the nature of software, functions described herein can be implemented using software executed by a processing system, hardware, firmware, hardwiring, or combinations of any of these. Features implementing functions may be physically located at various positions, including being distributed such that portions of functions are implemented at different physical locations.

FIG. 23 shows a flowchart illustrating a method 2300 that supports nerve modulation in accordance with examples as disclosed herein. The operations of method 2300 may be implemented by a substrate 101 or its components as described herein. For example, the operations of method 2300 may be performed by a substrate as described with reference to FIGS. 1 through 22. In some examples, a substrate may execute a set of instructions to control the functional elements of the device to perform the described functions. Additionally, or alternatively, the substrate may perform aspects of the described functions using special-purpose hardware.

At 2305, a system may be provided. The system may include a substrate that includes a first polymer layer with plurality of embedded electrodes coupled with an interconnect via conductive ink, a second polymer layer, and a liner molded to the second polymer layer, the substrate and the liner configured to receive and attach to the residual limb such that the plurality of electrodes are in electrical communication with the residual limb.

At 2310, the method may include transmitting, with an electrode controller in electrical communication with each electrode via the interconnect, electrical current through the residual limb.

At 2315, the method may include stimulating nerve fibers in the residual limb responsive to transmitting electrical current with the plurality of electrodes.

FIG. 24 shows a flowchart illustrating a method 2400 that supports nerve modulation in accordance with examples as disclosed herein. The operations of method 2400 may be implemented by a substrate 101 or its components as described herein. For example, the operations of method 2400 may be performed by a substrate as described with reference to FIGS. 1 through 22. In some examples, a substrate may execute a set of instructions to control the functional elements of the device to perform the described functions. Additionally, or alternatively, the substrate may perform aspects of the described functions using special-purpose hardware.

At 2405, a system may be provided. The system may include a substrate that includes a first polymer layer including a plurality of electrodes coupled with a plurality of conductive traces comprising conductive ink, and a second polymer layer, where the substrate is configured to attach to a user's skin such that the plurality of electrodes is in electrical communication with the user's skin.

At 2410, the method may include transmitting, with an electrode controller in electrical communication with each electrode via an interconnect coupled with the electrode controller and the plurality of conductive traces, electrical current through the user's skin.

At 2415, the method may include stimulating nerve fibers in the user's skin responsive to transmitting electrical current with the plurality of electrodes.

The disclosed methods include methods of treating acute symptoms and reducing chronic symptoms. Treating an acute symptom refers to treating a symptom while a subject experiences the symptom, and acute efficacy refers to real-time efficacy at alleviating the acute symptom.

Reducing chronic symptoms refers to reducing one or both of the frequency and severity of the symptom over time. Reducing chronic symptoms, for example of phantom limb pain, phantom limb syndrome, residual limb pain, general soreness, muscular atrophy, or pain-related impairment, independent from treating acute symptoms refers to reducing one or both of the frequency and severity of the symptom over time independent from treating an acute symptom; for example, after using a system described herein for a period of time (such as a course of at least 28 days), a subject may find that he or she experiences less frequent symptoms of phantom limb syndrome and that the symptoms are less severe independent from whether the subject actually treats any given symptom with the system.

Each amputee has a brain that comprises a somatosensory cortex. In some embodiments, the method is effective to activate different areas of the somatosensory cortex when different electrodes transmit and receive electrical current to and from the residual limb.

Without limiting this specification or any patent claim that matures from this disclosure, repeated use of the systems of this disclosure reduces chronic symptoms by neuromodulation in the somatosensory cortex.

The somatosensory cortex of the brain of an amputee typically includes a region for processing sensations of the missing body part. In some embodiments, the method comprises transmitting electrical current through the residual limb from electrodes periodically over a period of time such as a course of at least 28 days; and the method is effective to cause neuromodulation such that the electrical current causes activation in the region for processing sensations of the missing body part following the period of time. In some specific embodiments, the method comprises transmitting electrical current through the residual limb from a corresponding two or more electrodes periodically over the period of time; and the method is effective to cause neuromodulation such that the electrical current causes activation in the region for processing sensations of the missing body part following the period of time.

In some embodiments, an array of electrodes is configured in the substrate such that each electrode is a paired electrode that can be paired with at least one other electrode of the array of electrodes, wherein, when the array of electrodes is in electrical communication with the residual limb, then each paired electrode can (1) transmit electrical current through the residual limb to a negative electrode with which the paired electrode is paired and/or (2) receive electrical current through the residual limb from a positive electrode with which the paired electrode is paired. In some specific embodiments, the electrodes are configured in the polymer liner such that each electrode is a paired electrode that can be paired with at least two other electrodes of the electrodes such that, when the electrodes are in electrical communication with the residual limb, then each paired electrode can (1) transmit electrical current through the residual limb both to a first negative electrode with which the paired electrode is paired and, independently, to a second negative electrode with which the paired electrode is paired and/or (2) receive electrical current through the residual limb from both a first positive electrode with which the paired electrode is paired and, independently, from a second positive electrode with which the paired electrode is paired.

In some embodiments, the array of electrodes is configured such that when (1) two or more electrodes of the array of electrodes are activated and (2) the two or more electrodes are in electrical communication with the residual limb, then one activated electrode of the activated two or more electrodes transmits electrical current through the residual limb and another activated electrode of the activated two or more electrodes receives the electrical current that is transmitted through the residual limb.

In some embodiments, the liner is a product produced by a process in which (a) a substrate comprising the wires and the electrodes is placed in a mold and (b) liquid polymer is then poured into the mold such that the wires and the array of electrodes become embedded in the polymer thereby producing the liner. For example, the liner may be a polymer liner produced by pouring liquid polymer or monomers thereof into the mold.

In some embodiments, the substrate is a polymer that comprises a polymer selected from silicone, polyurethane, and thermoplastic elastomer. In some embodiments, the liner is a polymer liner that comprises a polymer selected from silicone, polyurethane, and thermoplastic elastomer. Selecting a substrate polymer compatible with a liner polymer results in better fusion between the substrate and liner and avoids space delamination.

In some embodiments, each electrode is a stimulating electrode that is configured to transmit and/or receive electrical current that stimulates neurons in the residual limb when the stimulating electrode is in electrical communication with the residual limb. Suitable stimulating electrodes include, for example, carbon rubber electrodes.

Other example user devices may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

The electronic devices associated with the user may include one or more of the following functionalities: 1) measuring physiological data, 2) storing measured data, 3) processing data, 4) providing outputs (e.g., via GUIs) to a user based on the processed data, and 5) communicating data with one another and/or other computing devices. Different electronic devices may perform one or more of the functionalities.

Some electronic devices may measure physiological parameters of a user, such as photoplethysmography waveforms, continuous skin temperature, a pulse waveform, respiration rate, heart rate, heart rate variability (HRV), actigraphy, galvanic skin response, pulse oximetry, blood oxygen saturation ($SpO_2$), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a mobile device application, or a server computing device may process received physiological data that was measured by other devices.

In some implementations, a user may operate, or may be associated with, multiple electronic devices, some of which may measure physiological parameters and some of which may process the measured physiological parameters. In some implementations, a user may have an electronic device that measures physiological parameters. The user may also have, or be associated with, a user device (e.g., mobile device, smartphone), where the electronic device and the user device are communicatively coupled to one another. In some cases, the user device may receive data from the electronic device and perform some/all of the calculations described herein. In some implementations, the user device may also measure physiological parameters described herein, such as motion/activity parameters.

In some embodiments, the systems include modulating nerve activation in a residual limb of an amputee with a user interface configured to receive an input from the amputee and display an output; a processor, memory in electronic communication with the processor; and instructions stored in the memory and executable by the processor to cause the apparatus to: transmit, with an electrode controller in electrical communication with an electrode in a prosthetic liner substrate, electrical current through the residual limb; and stimulate Aβ nerve fibers in the residual limb responsive to transmitting electrical current with the electrode.

In some embodiments, the disclosed technology includes non-transitory computer-readable medium comprising instructions to cause a processor to: transmit with an electrode controller in electrical communication with an electrode in a prosthetic liner substrate, electrical current through a residual limb of an amputee; and stimulate Aβ nerve fibers in the residual limb responsive to transmitting electrical current with the electrode. The processor may be further configured to detect physiological parameters with at least one sensor; measure physiological data from the physiological parameters; store the measured physiological data; process the measured physiological data; and provide outputs to a user or other computing device responsive to processing the measured physiological data.

It should be noted that the methods described above describe possible implementations, and that the operations and the steps may be rearranged, omitted, or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid space obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations.

Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

As used herein, including in the claims, the article "a" before a noun is open-ended and understood to refer to "at least one" of those nouns or "one or more" of those nouns. Thus, the terms "a," "at least one," "one or more," "at least one of one or more" may be interchangeable. For example, if a claim recites "a component" that performs one or more functions, each of the individual functions may be performed by a single component or by any combination of multiple components. Thus, the term "a component" having characteristics or performing functions may refer to "at least one of one or more components" having a particular characteristic or performing a particular function. Subsequent reference to a component introduced with the article "a" using the terms "the" or "said" may refer to any or all of the one or more components. For example, a component introduced with the article "a" may be understood to mean "one or more components," and referring to "the component" subsequently in the claims may be understood to be equivalent to referring to "at least one of the one or more components." Similarly, subsequent reference to a component introduced as "one or more components" using the terms "the" or "said" may refer to any or all of the one or more components. For example, referring to "the one or more components" subsequently in the claims may be understood to be equivalent to referring to "at least one of the one or more components."

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

The invention claimed is:

1. A system for modulating nerve activation in a residual limb of an amputee, comprising:
   a substrate including a plurality of electrodes and a plurality of conductors coupled with each of the plurality of electrodes, the substrate configured to receive and contact the residual limb such that at least one of the plurality of electrodes is in electrical communication with the residual limb at one or more locations;
   an electrode controller configured to transmit electrical current to the plurality of electrodes according to a first input;
   an interconnect configured for an amputee to interchangeably connect the electrode controller and the substrate when coupled with the conductors; and
   an external user device to communicate signaling with the electrode controller, including:
      a graphical user interface configured to receive the first input from the amputee, wherein the first input corresponds to directly and selectively activating one or more of the plurality of electrodes at the one or more locations such that nerve fibers are stimulated in the residual limb.

2. The system of claim 1, further comprising:
   a prosthetic liner.

3. The system of claim 1, wherein at least one of the substrate, the interconnect, and the conductors include flexible material.

4. The system of claim 1, wherein the substrate includes at least one of a cooling material, a moisture wicking material, an antimicrobial material, an antibacterial material or a combination thereof.

5. The system of claim 1, wherein a second input corresponds to selecting a first sensation such that the selectively activated electrodes electrically stimulate the nerve fibers in the residual limb with the first sensation.

6. The system of claim 5, wherein the first sensation is selected from tapping sensation, a kneading sensation, a rolling sensation, a cupping sensation, or a scraping sensation.

7. The system of claim 6, wherein a third input corresponds to user feedback from the amputee, selected from pain feedback, mental health feedback, or preferred setting feedback.

8. The system of claim 1, wherein the plurality of electrodes for stimulating nerve fibers in the amputee's skin may be selected by an artificial intelligence algorithm.

9. The system of claim 8, wherein a second input corresponds to user feedback from the amputee and the second input is configured to provide data to personalize the artificial intelligence algorithm to the amputee.

10. The system of claim 1, wherein a thickness of the substrate is 26 mm or less.

11. The system of claim 1, wherein the substrate is stretchable and the conductors are configured to communicate the signaling to each electrode from the interconnect and communicate the signaling to the interconnect from each electrode when the substrate is stretched in any direction.

12. The system of claim 1, wherein the substrate comprises one or more sensors in communication with the residual limb and configured to receive one or more parameters associated with substrate, the residual limb, or a combination thereof.

13. The system of claim 12, wherein the substrate further comprises one or more feedback paths for the one or more sensors.

14. The system of claim 12, wherein the one or more sensors comprise a stretch sensor, a temperature sensor, a movement sensor, a motion sensor, a moisture sensor, an oxygen sensor, a pressure sensor, a bacterial sensor, a vibrational sensor, a blood glucose sensor, a pulse oxygen sensor, a magnetic flux sensor, or a combination thereof.

15. The system of claim 14, wherein:
   the stretch sensor comprises a piezo resistive sensor;
   the movement sensor comprises an accelerometer, a gyroscope, an optical sensor, a hall effect sensor, or a resistive flexion sensor;
   the oxygen sensor comprises an optical oximeter;
   the pressure sensor comprises a capacitive sensor, a force sensing resistor, an optical sensor, a pneumatic sensor, a strain-gauge sensor, a piezoelectric sensor, or a piezo chromic sensor; and
   the vibrational sensor comprises an accelerometer or a gyroscope.

16. The system of claim 1, wherein the conductors comprise silver infused nanoparticles, gold infused nanoparticles, a silver coated material, a conductive carbon material, or a combination thereof.

17. The system of claim 1, wherein the interconnect is configured as a connection for connecting with a power source.

18. The system of claim 1, wherein the external user device is a mobile device, a computer, or a wearable device.

19. The system of claim 1, wherein the substrate comprises a plurality of traces that comprise the conductors, wherein each electrode of the plurality of electrodes is coupled with a respective trace, and wherein the plurality of traces each terminate at an end of the substrate and are configured to connect to the interconnect.

20. A system for modulating nerve activation in a residual limb of an amputee, comprising:
   a substrate configured to contact the residual limb, including a plurality of electrodes and a plurality of conductors coupled with each of the plurality of electrodes;
   an electrode controller configured to transmit electrical current to the plurality of electrodes according to one or more inputs;
   an interconnect configured for an amputee to interchangeably connect the electrode controller and the substrate when coupled with the conductors; and
   an external user device to communicate wireless signaling with the electrode controller, the external user device selected from a mobile phone, a computer, or a wearable device, and including:
      a graphical user interface configured to receive a first input of the one or more inputs from the amputee, wherein the first input corresponds to directly and selectively activating one or more of the plurality of electrodes such that nerve fibers are stimulated at one or more locations in the residual limb, wherein a second input corresponds to selecting a first sensation selected from tapping sensation, a kneading sensation, a rolling sensation, a cupping sensation, or a scraping sensation such that the selectively activated electrodes stimulate the nerve fibers in the residual limb at the one or more locations with the first sensation, and wherein a third input corresponds to user feedback from the amputee, selected from pain feedback, mental health feedback, and preferred setting feedback.

\* \* \* \* \*